US012667347B2

(12) United States Patent (10) Patent No.: US 12,667,347 B2

Nakamura (45) Date of Patent: Jun. 30, 2026

(54) MEDICAL STAPLER AND MEDICAL SYSTEM

(71) Applicant: OLYMPUS CORPORATION, Tokyo (JP)

(72) Inventor: Takashi Nakamura, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 400 days.

(21) Appl. No.: 18/337,236

(22) Filed: Jun. 19, 2023

(65) Prior Publication Data

US 2023/0329684 A1 Oct. 19, 2023

Related U.S. Application Data

(63) Continuation of application No. PCT/JP2020/048476, filed on Dec. 24, 2020.

(51) Int. Cl.
*A61B 17/00* (2006.01)
*A61B 1/00* (2006.01)
(Continued)

(52) U.S. Cl.
CPC .......... *A61B 17/00* (2013.01); *A61B 1/00195* (2013.01); *A61B 2017/00318* (2013.01);
(Continued)

(58) Field of Classification Search
CPC .......... A61B 17/00; A61B 2017/00318; A61B 1/00195; A61B 1/00137; A61B 17/2841;
(Continued)

(56) References Cited

U.S. PATENT DOCUMENTS 4,655,219 A * 4/1987 Petruzzi ............. A61B 17/2909
606/206
5,569,299 A * 10/1996 Dill ........................ A61B 10/06
606/208
(Continued)

FOREIGN PATENT DOCUMENTS

JP 1147079 A 2/1999
JP 2004503325 A 2/2004
(Continued)

OTHER PUBLICATIONS

"International Application Serial No. PCT/JP2020/048476, International Search Report dated Mar. 2, 2021", w/ English Translation, (Mar. 2, 2021).

*Primary Examiner* — Michael J Carey
(74) *Attorney, Agent, or Firm* — Schwegman Lundberg & Woessner, P.A.

(57) ABSTRACT

A medical stapler includes a grasping portion connected to an endoscope and having a first jaw and a second jaw connected by a rotation shaft; an operation portion configured to receive an external force for operating the grasping portion to open and close; a first wire configured to transmit the external force that is received by the operation portion to the grasping portion; and a movable pin attached to a distal end of the first wire, wherein the grasping portion is transitioned to an open state and a closed state by the first/second jaw relatively rotating with each other, and the movable pin is advanceable and retractable between positions at the proximal-end and distal-end side of the rotation shaft in a state in which the movable pin is engaged with an engagement groove formed in the first jaw.

20 Claims, 14 Drawing Sheets

(51) Int. Cl.
    *A61B 17/29*        (2006.01)
    *A61B 17/072*      (2006.01)

(52) U.S. Cl.
    CPC ............... *A61B 2017/00367* (2013.01); *A61B 2017/07221* (2013.01); *A61B 2017/2936* (2013.01)

(58) Field of Classification Search
    CPC .............. A61B 17/2909; A61B 1/0014; A61B 2017/00296; A61B 2017/2933; A61B 2017/2936
    See application file for complete search history.

(56)                  References Cited

U.S. PATENT DOCUMENTS

| | | | |
|---|---|---|---|
| 5,683,413 A * | 11/1997 | Miyagi .............. | A61B 1/00137 |
| | | | 606/208 |
| 6,059,719 A | 5/2000 | Yamamoto et al. | |
| 2002/0165444 A1 | 11/2002 | Whitman | |
| 2002/0173786 A1 | 11/2002 | Kortenbach et al. | |
| 2004/0034369 A1* | 2/2004 | Sauer .................... | A61B 1/012 |
| | | | 606/139 |
| 2004/0084497 A1 | 5/2004 | Aranyi | |
| 2011/0218400 A1 | 9/2011 | Ma et al. | |
| 2012/0143002 A1 | 6/2012 | Aranyi et al. | |

FOREIGN PATENT DOCUMENTS

| | | |
|---|---|---|
| JP | 2008188440 A | 8/2008 |
| JP | 2013132559 A | 7/2013 |
| JP | 2015221226 A | 12/2015 |
| WO | WO-0205721 A2 | 1/2002 |

* cited by examiner

MEDICAL STAPLER AND MEDICAL SYSTEM

The present application is a continuation application of PCT International Application No. PCT/JP2020/048476, filed on Dec. 24, 2020. The content of the above-identified PCT International Applications is incorporated herein by reference.

TECHNICAL FIELD

The present disclosure relates to a medical stapler and a medical system.

BACKGROUND ART

In recent years, the surgery to suture the gastrointestinal tract or the like using a medical stapler is known. It is possible to facilitate the operations to suture the gastrointestinal tract or the like and significantly shorten the operation period by using the suitable medical stapler.

A full-thickness resection system disclosed in Published Japanese Translation No. 2004-503325 of the PCT International Publication includes an endoscope and a stapling mechanism arranged in the surrounding of the endoscope. The full-thickness resection system is configured to observe the treatment target by the endoscope while performing the suturing treatment with respect to the treatment target by the stapling mechanism.

SUMMARY

According to an aspect of the present disclosure, a medical stapler, includes a grasping portion connected to an endoscope and having a first jaw and a second jaw connected by a rotation shaft; an operation portion configured to receive an external force for operating the grasping portion to open and close; a first wire including a proximal end connected with the operation portion and a distal end connected with the grasping portion and configured to transmit the external force that is received by the operation portion to the grasping portion; and a movable pin attached to the distal end of the first wire. The grasping portion is transitioned to an open state and a closed state by the first jaw and the second jaw relatively rotating with the rotation shaft as a rotation center due to the external force transmitted by the first wire. The rotation shaft is positioned at a distal-end side of a distal end of the endoscope along a longitudinal direction of the endoscope. The movable pin is advanceable and retractable between a position at the proximal-end side of the rotation shaft and a position at the distal-end side of the rotation shaft along the longitudinal direction in a state in which the movable pin is engaged with an engagement groove formed in the first jaw. A first tangent in a contact portion of the first jaw and the movable pin and a second tangent in a contact portion of the second jaw and the movable pin are inclined with each other at a slide angle $\theta$, and the slide angle $\theta$ is determined by an equation, wherein the value $\mu$ is a friction coefficient between the first jaw or the second jaw and the movable pin.

$$\tan \theta > 2*\mu \tag{3}$$

According to another aspect of the present disclosure, a medical system includes an endoscope having flexibility; and a medical stapler engaged with the endoscope, wherein the medical stapler includes a grasping portion connected to an endoscope and having a first jaw and a second jaw connected by a rotation shaft; an operation portion configured to receive an external force for operating the grasping portion to open and close; a first wire including a proximal end connected with the operation portion and a distal end connected with the grasping portion and configured to transmit the external force that is received by the operation portion to the grasping portion; and a movable pin attached to the distal end of the first wire. The grasping portion is transitioned to an open state and a closed state by the first jaw and the second jaw relatively rotating with the rotation shaft as a rotation center due to the external force transmitted by the first wire. The rotation shaft is positioned at a distal-end side of a distal end of the endoscope along a longitudinal direction of the endoscope. The movable pin is advanceable and retractable between a position at the proximal-end side of the rotation shaft and a position at the distal-end side of the rotation shaft along the longitudinal direction in a state in which the movable pin is engaged with an engagement groove formed in the first jaw. A first tangent in a contact portion of the first jaw and the movable pin and a second tangent in a contact portion of the second jaw and the movable pin are inclined with each other at a slide angle $\theta$, and the slide angle $\theta$ is determined by an equation, wherein the value $\mu$ is a friction coefficient between the first jaw or the second jaw and the movable pin.

$$\tan \theta > 2*\mu \tag{3}$$

BRIEF DESCRIPTION OF DRAWINGS

FIG. 9 is a side view showing the medical stapler in which the grasping portion is in the open state.

FIG. 10 is a cross-sectional view showing the grasping portion including a staple extraction portion.

FIG. 25 is a view showing a configuration in which a cap of the medical stapler according to the present embodiment is attached to an endoscope.

DESCRIPTION OF EMBODIMENTS

First Embodiment

A first embodiment of the present disclosure will be described referring from FIG. 1 to FIG. 15.

Figure 1:
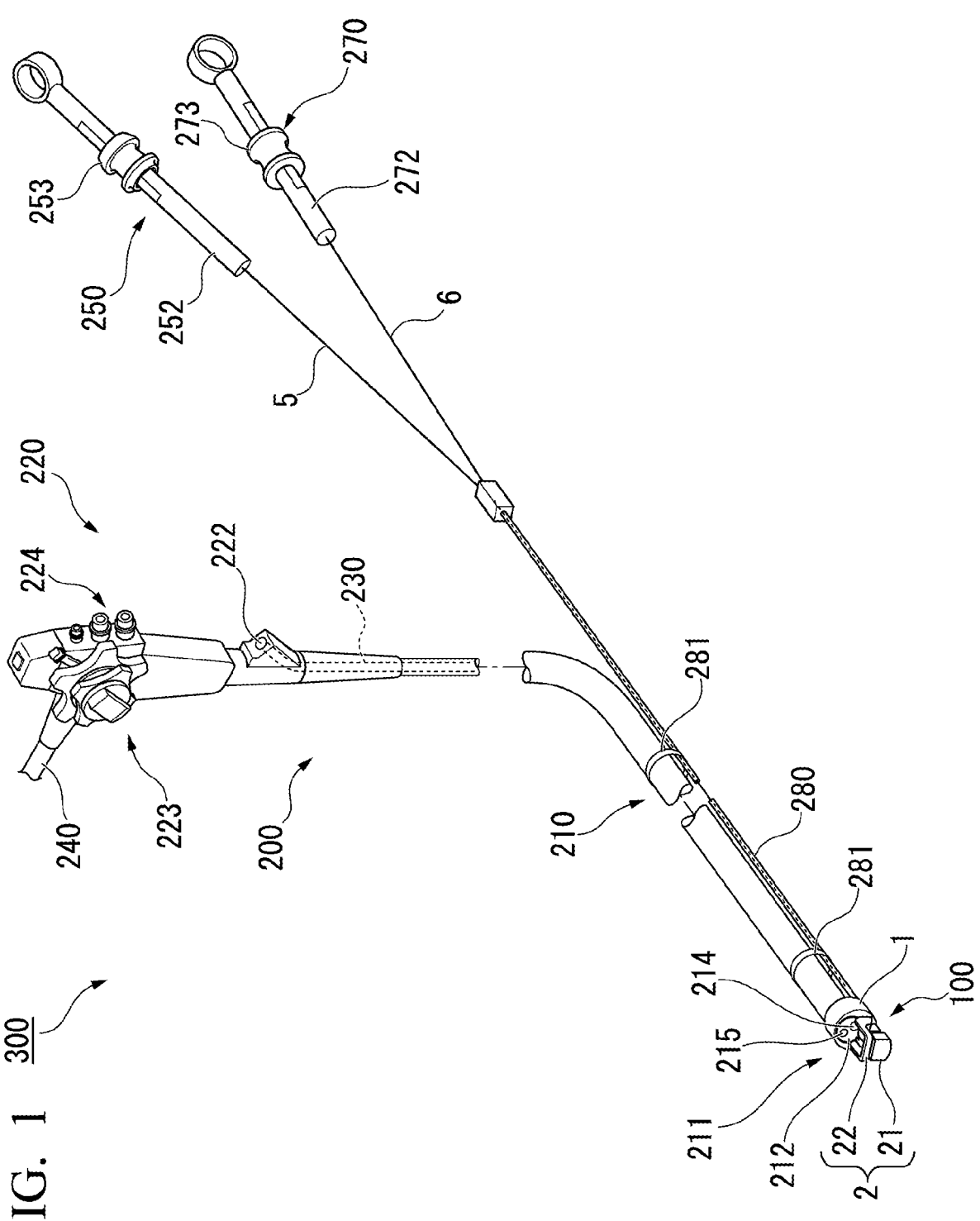
FIG. 1 is a view showing a medical system including a medical stapler according to a first embodiment of the present disclosure.

FIG. 1 is a view showing an overall configuration of a medical system 300 including a medical stapler 100 according to the present embodiment.

[Medical System 300]

The medical system 300 is used in the surgery for suturing the gastrointestinal tract or the like of a patient. As shown in FIG. 1, the medical system 300 includes the medical stapler 100, an endoscope 200, an open-close operation portion (first operation portion) 250, an extraction operation portion (second operation portion) 270, and a wire sheath 280. The open-close operation portion 250 is an operation portion for operating the medical stapler 100 by an open-close operation wire (first wire) 5. The extraction operation portion 270 is an operation portion for operating the medical stapler 100 by an extraction operation wire (second wire) 6.

[Endoscope 200]

As shown in FIG. 1, the endoscope 200 includes an insertion portion 210, an endoscope operation portion (third operation portion) 220, and a universal cord 240. The insertion portion 210 is an elongated member inserted into the body of the patient from a distal end thereof. The endoscope operation portion 220 is provided at a proximal-end portion of the insertion portion 210. The endoscope 200 is suitably configured using a conventional flexible endoscope.

As shown in FIG. 1, the insertion portion 210 is formed with a treatment device channel 230 through which the endoscopic treatment device is inserted. At a distal end 212 of the insertion portion 210, a forceps port 214 as a distal-end opening of the treatment device channel 230 is provided. The treatment device channel 230 extends from the distal end 212 of the insertion portion 210 to the endoscope operation portion 220. The distal end 212 of the insertion portion 210 refers to a plane at the most distal-end side in a distal-end portion 211 of the insertion portion 210 along the longitudinal direction of the endoscope 200.

The distal-end portion 211 of the insertion portion 210 includes an imaging unit (not shown) including an imaging element such as a CCD, a CMOS or the like and configured to acquire images or videos of the treatment target T described below. An objective lens 215 of the imaging unit is exposed from the distal end 212 of the insertion portion 210.

At the proximal-end side of the endoscope operation portion 220, a knob 223 for the surgeon to operate the insertion portion 210 and a switch 224 for operating the imaging unit or the like are provided. The surgeon can bend the insertion portion 210 to a desired direction by operating the knob 220.

At the distal-end side of the endoscope operation portion 220, a forceps insertion port 222 communicating with the treatment device 230 is provided. The surgeon can insert the endoscopic treatment device into the treatment device channel 230 from the forceps insertion port 222.

The universal cord 240 connects the endoscope operation portion 220 and external peripheral devices. For example, the universal cord 240 outputs the images captured by the imaging unit to the external devices. The image captured by the imaging unit is displayed on a display device such as an LCD display or the like.

[Open-Close Operation Portion 250]

Figure 7:
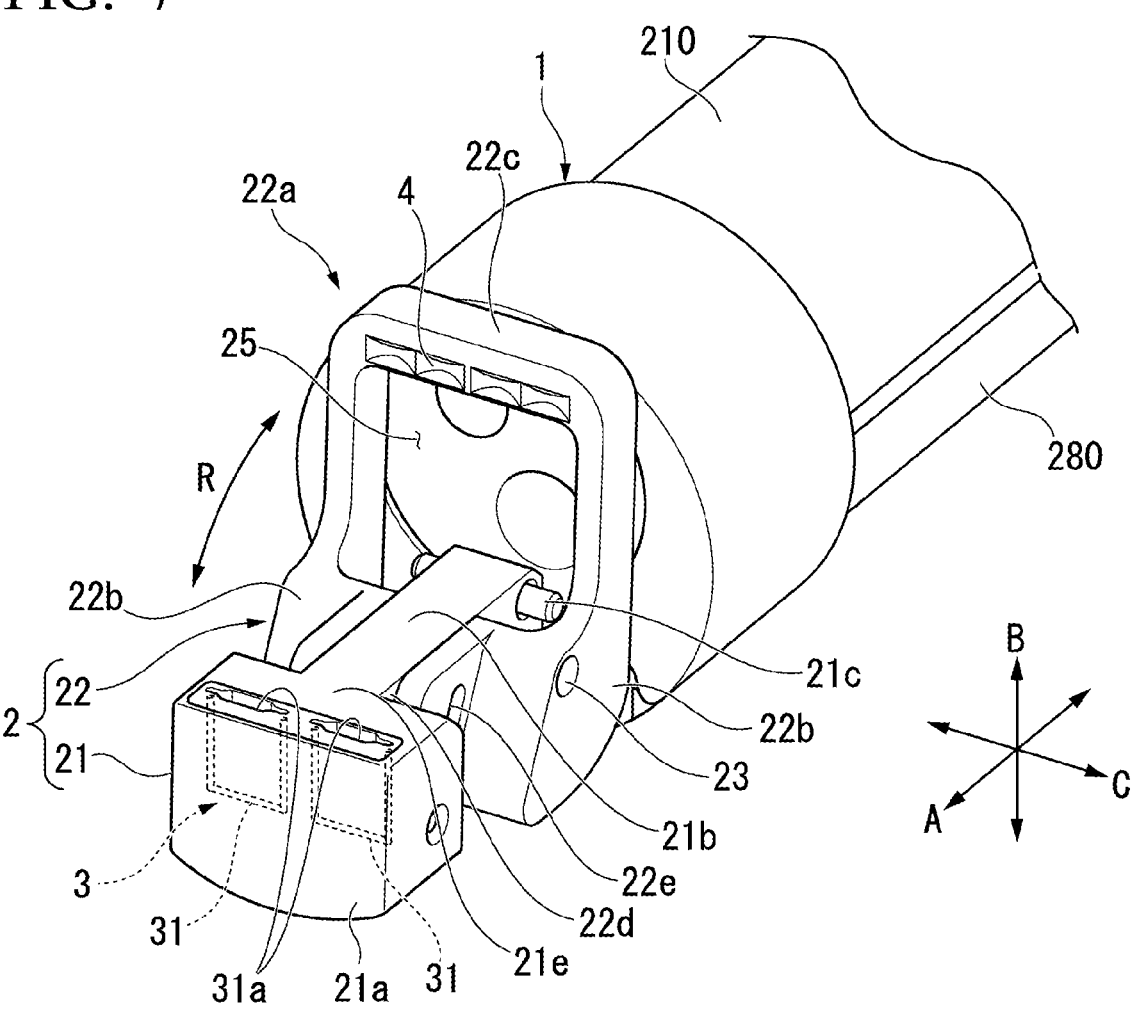
FIG. 7 is a perspective view showing the medical stapler in which the grasping portion is in an open state.

The open-close operation portion (first operation portion) 250 is an operation portion for the surgeon to open and close the medical stapler 100 by operating the open-close operation wire (first wire) 5. As shown in FIG. 1, the open-close operation portion 250 includes an open-close operation portion main body 252 and an open-close operation slider 253. The open-close operation slider 253 is connected with a proximal end of the open-close operation wire 5. The open-close operation wire 5 has the rigidity for transmitting the force by the surgeon to press the open-close operation slider 253 to the medical stapler 100 so as to open the first grasping member (first jaw) 21 and the second grasping member (second jaw) 22. It is possible for the surgeon to advance and retract the open-close operation wire 5 by advancing and retracting the open-close operation slider 253 with respect to the open-close operation portion main body 252 along the longitudinal direction. More specifically, when the surgeon presses the open-close operation slider 253, the open-close operation wire 5 advances into a predetermined region (first region) along the longitudinal direction and the medical stapler 100 described below enters the open state. The first grasping member 21 and the second grasping member 22 of the medical stapler 100 relatively rotates with the open-close rotation shaft 23 as the rotation center such that the first grasping member 21 and the second grasping member 22 are separated from each other and the medical stapler 100 enters the open state. In the present embodiment, the open state of the medical stapler 100 includes a state in which the first grasping member 21 and the second grasping member 22 are opened at substantially 90 degrees, as shown in FIG. 7.

Figure 6:
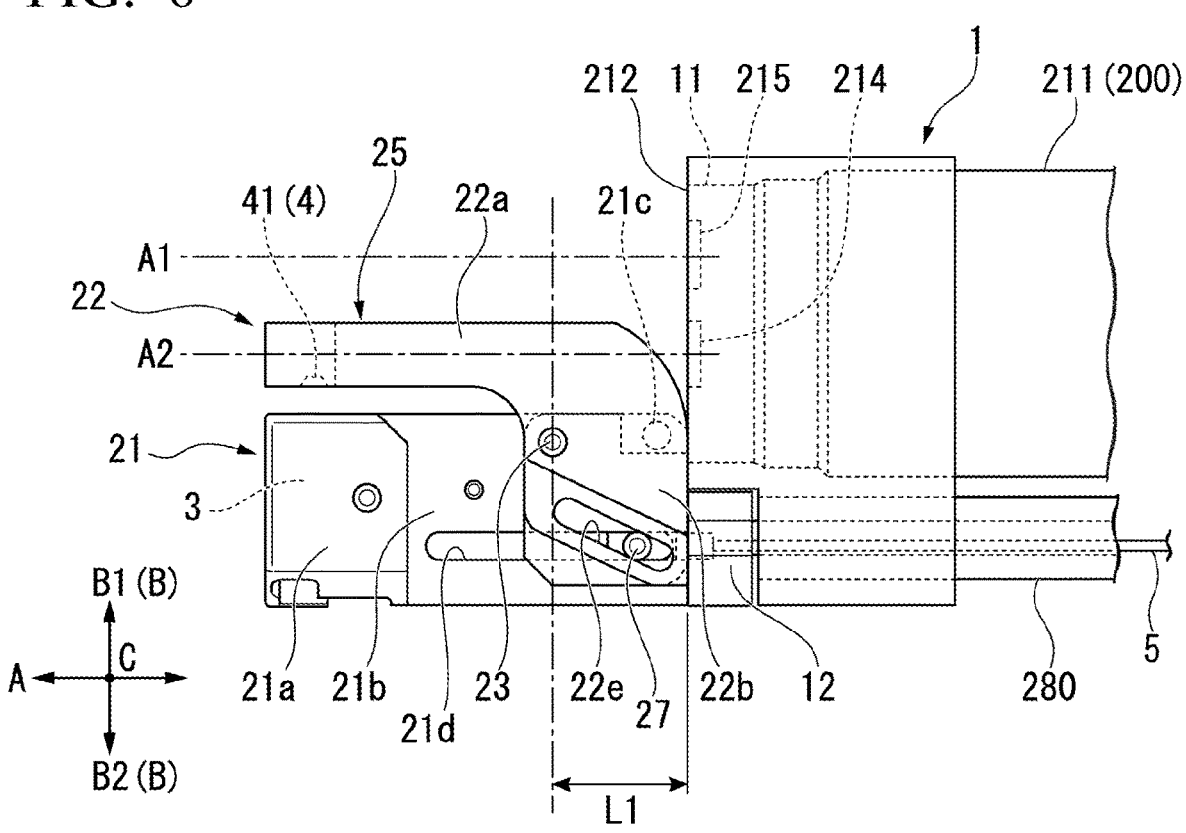
FIG. 6 is a side view showing the medical stapler in which the grasping portion is in the closed state.

When the surgeon pulls the open-close operation slider 253, the open-close operation wire 5 retracts into the predetermined region (first region) along the longitudinal direction and the medical stapler 100 are closed to enter the closed state. When the open-close operation wire 5 retracts along the longitudinal direction, the first grasping member 21 and the second grasping member 22 relatively rotates with the open-close rotation shaft 23 at the rotation center such that the first grasping member 21 and the second grasping member 22 approaches each other and the medial stapler 100 enters the closed state. In the present embodiment, the closed state of the medical stapler 100 refers to the state in which the first grasping member 21 and the second grasping member 22 included in the medical stapler 100 are opposite to each other in the up-down direction B and to approach each other. The closed state of the medical stapler 100 includes a state in which the first grasping member 21 and the second grasping member 22 are opposite to each other to be substantially parallel to each other and there is a gap formed therebetween, as shown in FIG. 6.

[Extraction Operation Portion 270]

The extraction operation portion (second operation portion) 270 is an operation portion for the surgeon to extract the staple S from the medical stapler 100 by operating the extraction operation wire (second wire) 6. As shown in FIG. 1, the extraction operation portion 270 includes an extraction operation portion main body 272 and an extraction operation slider 273. A proximal end of the extraction operation wire 6 is connected with the extraction operation slider 273. The surgeon can advance and retract the extraction operation wire 6 in a predetermined region (second region) along the longitudinal direction by advancing and retracting the extraction operation slider 273 with respect to the extraction operation portion main body 272 along the longitudinal direction. More specifically, in the present embodiment, when the surgeon pulls the extraction operation slider 273, as described below, the extraction operation wire 6 retracts into the predetermined region (second region) along the longitudinal direction and the staple S is extracted from the accommodation space. Also, when the surgeon releases the operation of pulling the extraction operation slider 273, the extraction operation wire 6 may advance into the predetermined region (second region) along the longitudinal direction and the staple S may be accommodated in a staple accommodation portion 31 (see FIG. 10).

[Wire Sheath 280]

Figure 25:
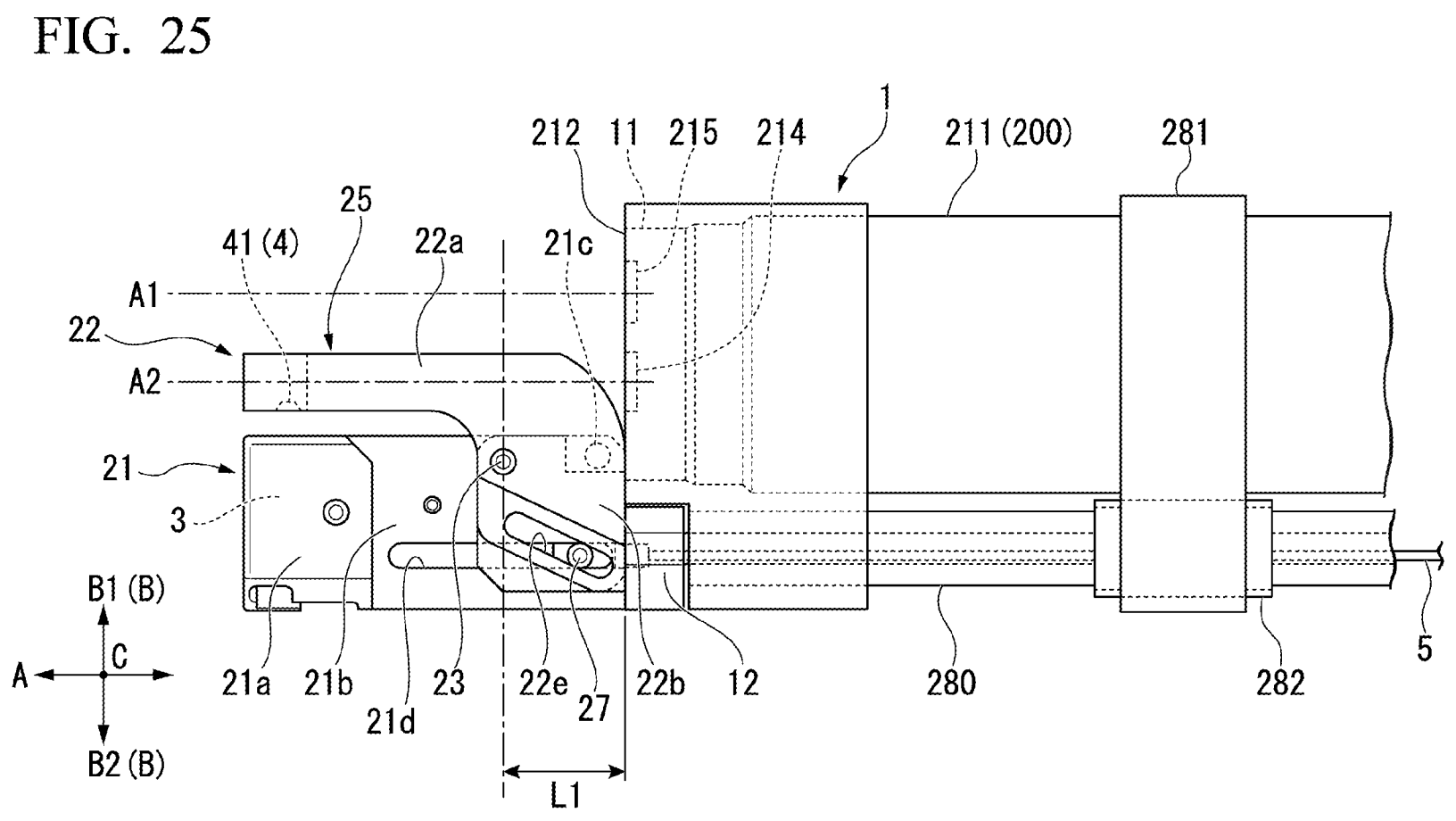

The wire sheath 280 is a sheath through which the open-close operation wire 5 and the extraction operation wire 6 are inserted. As shown in FIG. 1, the distal-end side of the wire sheath 280 is connected with the insertion portion 210 of the endoscope 200 by a band 281. An example of the configuration in which the endoscope 200 and the band 281 are connected with each other is shown in FIG. 25. As shown in FIG. 25, the band 281 and the endoscope 200 are fixed therewith. On the other hand, the wire sheath 280 formed in the material such as the resin or the like is not fixed to the band 281. The wire sheath 280 is provided to be slidable along the longitudinal direction and movable with respect to the band 281. According to the present configuration, the wire sheath 280 according to the present embodiment can slide following the bending operations of the endoscope 200.

[Medical Stapler 100]

Figure 2:
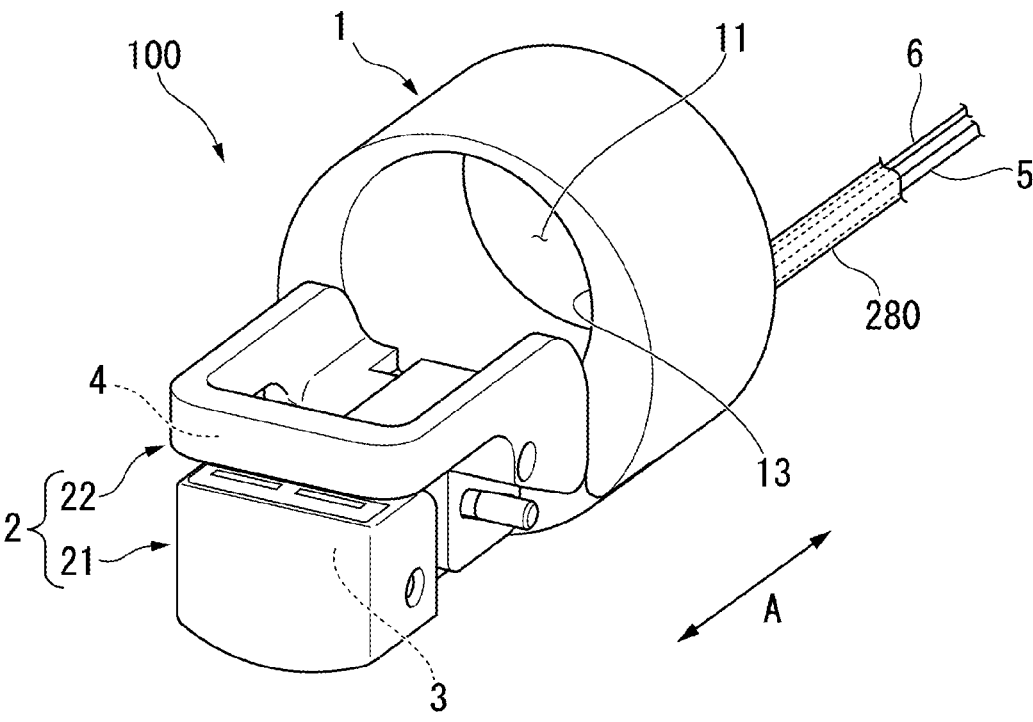
FIG. 2 is a perspective view showing the medical stapler.

FIG. 2 is a perspective view showing the medical stapler 100 according to the present embodiment.

The medical stapler 100 includes a cap 1, a grasping portion 2, a staple extraction portion 3, a staple reception portion 4, the open-close operation wire 5, and the extraction operation wire 6. The medical stapler 100 is attachable to and detachable from the distal end portion 211 of the insertion portion 210.

Figure 3:
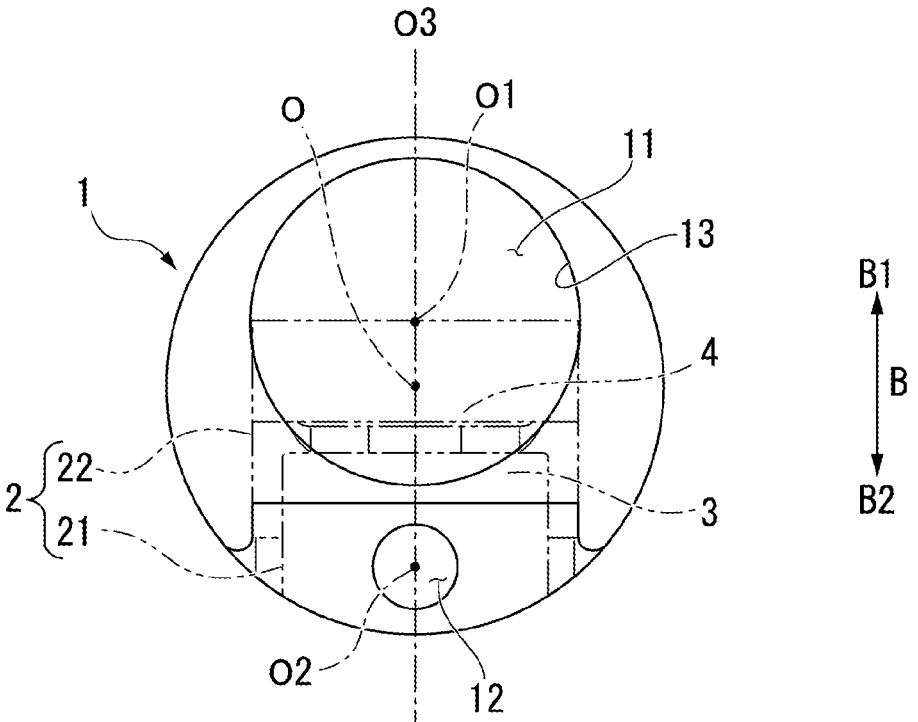
FIG. 3 is a front view showing a cap of the medical stapler.

FIG. 3 is a front view of the cap 1 viewed along the axial direction A. In FIG. 3, the grasping portion 2 is transparently displayed.

The cap (attachment-detachment portion) 1 is a member that is attachable to the distal-end portion 211 of the endoscope 200. The cap 1 is formed in an approximately cylindrical shape, and the cap 1 has a first penetration hole 11 penetrating in the axial direction A and a second penetration hole 12 penetrating in the axial direction A.

The first penetration hole 11 is a hole in which the distal-end portion 211 of the insertion portion 210 is inserted. The shape of the first penetration hole 11 is formed following the exterior shape of the distal-end portion 211 of the insertion portion 210. Accordingly, the distal-end portion 211 of the endoscope 200 is inserted into the first penetration hole 11 such that the cap 1 can be attached to the distal-end portion 211 of the endoscope 200.

The central axis O1 of the first penetration hole 11 in the axial direction A is eccentrical with respect to the central axis O of the cap 1 in the axial direction A, as shown in FIG. 3. The side in which the central axis O1 is eccentrical with respect to the central axis O is defined as an "upper side B1".

The second penetration hole 12 is a hole for the wire sheath 280 through which the open-close operation wire 5 and the extraction operation wire 6 are inserted to be inserted therein. An inner diameter of the second penetration hole 12 is approximately the same with the outer diameter of the wire sheath 280. The distal-end portion of the wire sheath 280 is inserted through the second penetration hole 12 to be fixed. The open-close operation wire 5 and the extraction operation wire 6 inserting through the wire sheath 280 pass through the second penetration hole 12 to extend to the distal-end side.

As shown in FIG. 3, the central axis O2 of the second penetration hole 12 in the axial direction A is eccentrical with respect to the central axis O of the cap 1 in the axial direction A. The direction in which the central axis O2 is eccentrical with respect to the central axis O is opposite to the side (upper side B1) in which the central axis O1 is eccentrical with respect to the central axis O. The side in which the central axis O2 is eccentrical with respect to the central axis O is defined as a "lower side B2". In the present embodiment, the upper side B1 and the lower side B2 are sides along the up-down direction B.

Figure 4:
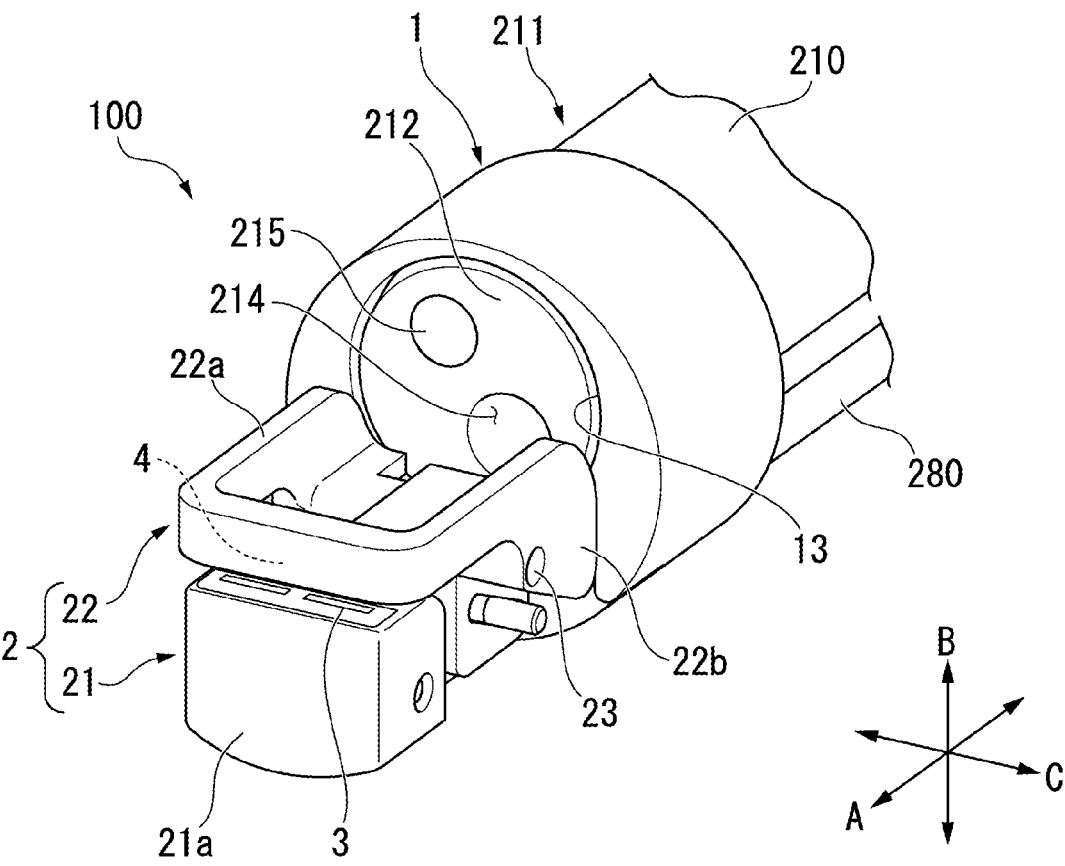
FIG. 4 is a perspective view showing the medical stapler in which a grasping portion is in a closed state.
Figure 5:
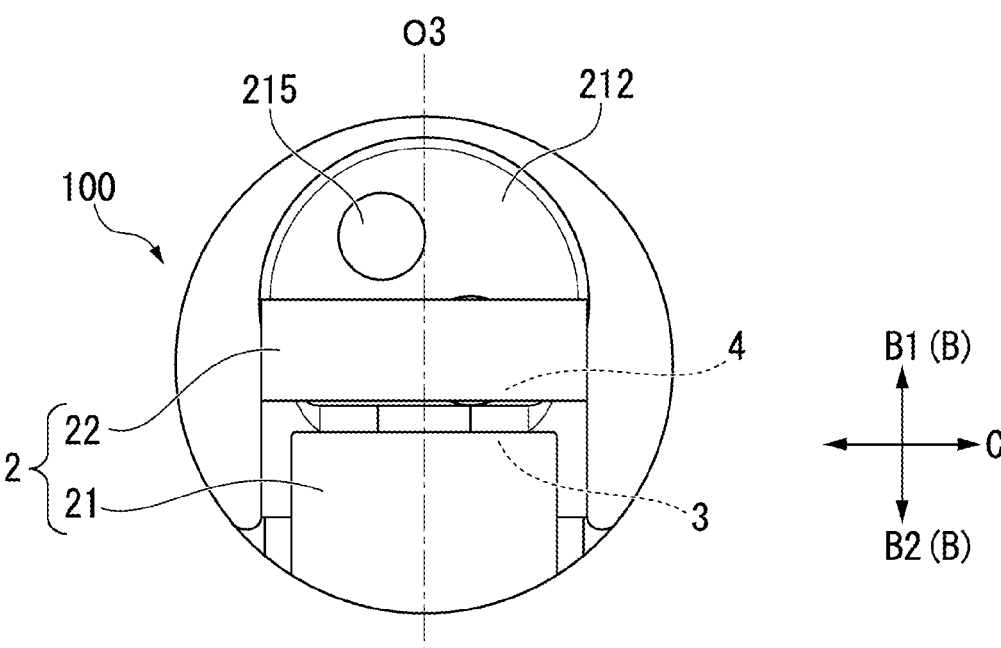
FIG. 5 is a front view showing the medical stapler in which the grasping portion is in the closed state.

FIG. 4, FIG. 5, and FIG. 6 are a perspective view, a front view, and a side view of the medical stapler 100 in which the grasping portion 2 is in the closed state, respectively.

As shown in FIG. 4, when the surgeon attaches the cap 1 to the endoscope 200, the medical stapler 100 is connected to the distal-end portion 211 of the insertion portion 210 of the endoscope 200 so as to be attachable to and detachable from the distal-end portion 211. When the cap 1 is attached to the distal-end portion 211 of the endoscope 200, as shown in FIG. 4 and FIG. 5, the objective lens 215 and the forceps port 214 are exposed from the opening 13 at the distal-end side in the first penetration hole 11 of the cap 1. The surgeon can observe the treatment target T by the objective lens 215 even if the medical stapler 100 is in the state of being attached to the distal-end portion 211 of the endoscope 200.

The medical stapler 100 according to the present embodiment is not limited to the configuration of using the cap 1 to be connected to the endoscope 200. It is possible to use variable conventional configurations to connect the medical stapler 100 to the endoscope 200. For example, it is possible to use a rubber band to connect the proximal-end portion of the medical stapler 100 to the endoscope 200. For example, it is possible to form a screw hole in the distal-end portion 211 of the insertion portion 210 of the endoscope 200, and then screw a screw into the screw hole formed in the distal-end portion 211 to attach and fix the medical stapler 100 to the distal-end portion 211 of the insertion portion 210 of the endoscope 200. Furthermore, it is possible to engage the medical stapler 100 and the endoscope 200 with each other by forming a convex portion and a concave portion, a locking mechanism or the like in the medical stapler 100 and the endoscope 200, respectively.

As shown in FIG. 5, when the grasping portion 2 is in the closed state, the staple extraction portion 3 and the staple reception portion 4 are opposite to each other. When the grasping portion 2 is in the closed state, a slightly narrow gap is formed between the staple extraction portion 3 and the staple reception portion 4. As shown in FIG. 4, FIG. 5, and FIG. 6, when the grasping portion 2 is in the closed state, the optical axis A1 of the objective lens 215 is positioned at the upper side B1 with respect to the first grasping member 21 and the second grasping member 22. Also, when the grasping portion 2 is in the closed state, the central axis A2 of the forceps port 214 does not overlap the first grasping member 21 in the front view; however, the central axis A2 of the forceps port 214 is at the position overlapping the second grasping member 22.

Figure 8:
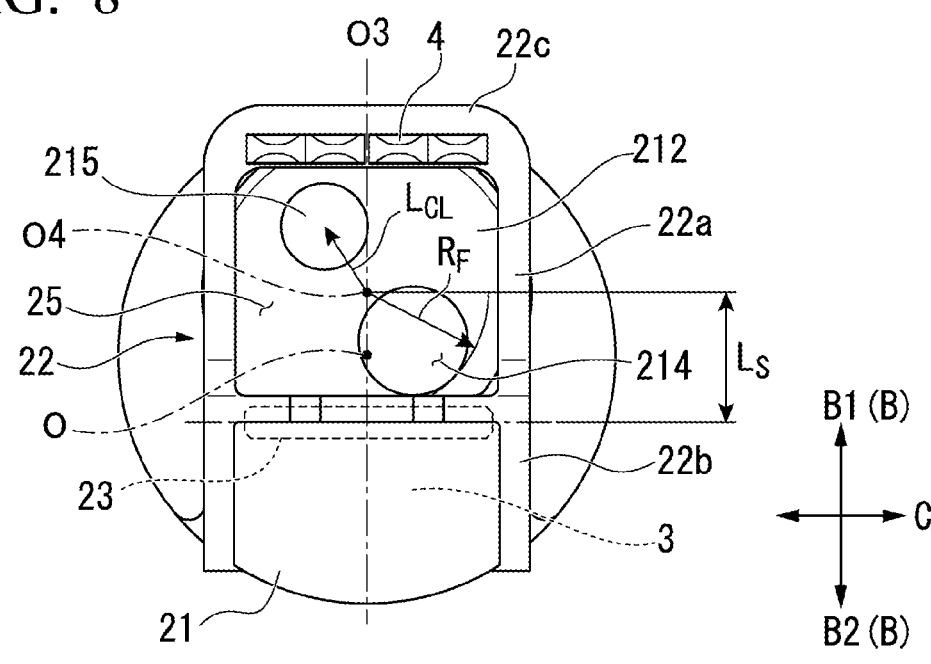
FIG. 8 is a front view showing the medical stapler in which the grasping portion is in the open state.

As shown in FIG. 6, the grasping portion 2 includes a first grasping member (first jaw) 21, a second grasping member (second jaw) 22, an open-close rotation shaft 23, and a movable pin 27. The first grasping member 21 and the second grasping member 22 are connected by the open-close rotation shaft 23 to be openable and closeable. In the present embodiment, the first grasping member 21 is configured to be rotatable with respect to the second grasping member 22 with the open-close rotation shaft 23 as the rotation center. The open-close rotation shaft 23 is provided at the distal-end side of the cap 1. More specifically, in the axial direction A, the open-close rotation shaft 23 is provided at the distal-end side than the distal end 212 of the insertion portion 210 of the endoscope 200. In FIG. 6, the open-close rotation shaft 23 and the distal end 212 of the endoscope 200 are separated from each other at a distance L1. The axial direction C of the open-close rotation shaft 23 is orthogonal to the axial direction A of the cap 1 and the up-down direction B. As shown in FIG. 8, the grasping portion 2 is symmetrically formed with respect to the central axis O3 in the up-down direction B.

As shown in FIG. 6, the first grasping member 21 includes a first distal-end portion 21a and a first main body portion 21b and is formed in a substantially T-shape in a planar view. The first distal-end portion 21a is arranged at the distal-end side than the first main body portion 21b.

The first distal-end portion 21a is formed in a substantially rectangular parallelepiped shape. The first distal-end portion 21a is formed in a rectangular shape extending in the axial direction C of the open-close rotation shaft 23 in the planar view. The first distal-end portion 21a is provided with the staple extraction portion 3. The opening 31a of the staple extraction portion 3 is provided on the surface (upper surface 21e) at the upper side B1 of the first distal-end portion 21a.

The first main body portion 21b is an elongated member extending in the axial direction A. The distal end of the first main body portion 21b is fixed to the first distal-end portion 21a. The proximal end of the first main body portion 21b is fixed to the cap 1. The first main body portion 21b includes a contact pin 21c and a first engagement groove 21d.

The contact pin 21c is provided at the proximal end of the first main body portion 21b, and the contact pin 21c is configured to come into contact with the second grasping member 22 in the closed state to regulate the moveable range of the second grasping member 22. More specifically, according to the present embodiment, when the grasping portion 2 is in the closed state, the distal-end portion of the first grasping member 21 and the distal-end portion of the second grasping member 22 are separated from each other by a predetermined distance or more. In other words, when the grasping portion 2 is in the closed state, a gap equal to or more than the predetermined distance is formed between the distal-end portion of the first grasping member 21 and the distal-end portion of the second grasping member 22. As described below, when the grasping portion 2 enters the closed state, the living tissues as the treatment target T is clamped between the first grasping member 21 and the second grasping member 22. Accordingly, if the gap formed in the grasping portion is too small, the crushing due to the grasping and the ischemia after the stapling may occur. Accordingly, in the present embodiment, the distance of the gap formed in the grasping portion 2 in the closed state is limited to be equal to or larger than the predetermined value by providing the contact pin 21c. In the present embodiment, the distance of the gap formed in the grasping portion 2 in the closed state may be appropriately determined by taking the type of the treatment target into consideration.

As shown in FIG. 6, the first engagement groove 21d is a groove penetrating in the axial direction C of the open-close rotation shaft 23 in the first main body portion 21b. The first engagement groove 21d extends in the axial direction A.

The second grasping member 22 is attached to the first grasping member 21 by the open-close rotation shaft 23 to be rotatable. The second grasping member 22 includes a U-shaped member 22a formed in a substantially U shape, and a second main body portion 22b rotatably supporting the U-shaped member 22a.

The U-shaped member 22a is formed in the substantially U-shape, wherein two end portions thereof are connected with the second main body portion 22b, and a central portion is arranged at the distal-end side. The central portion includes the second distal-end portion 22c. The second distal-end portion 22c is formed in the substantially rectangular parallelepiped shape. The second distal-end portion 22c is provided with the staple reception portion 4.

The second main body portion 22b is rotatably attached to the first main body portion 21b of the first grasping member 21 by the open-close rotation shaft 23. A guide groove 22d into which the first main body portion 21b is inserted is formed in the second main body portion 22b. The second engagement grooves 22e are formed in the two side portions of the guide groove 22d of the second main body portion 22b.

The second engagement groove 22e is a groove formed in the second main body portion 22b. The second engagement groove 22e is the groove penetrating in the axial direction C. In the side view, the second engagement groove 22e is formed at the opposite side of the staple reception portion 4 to sandwich the open-close rotation shaft 23 therebetween. The second engagement groove 22e is symmetrical with respect to the central axis O3 of the second grasping member 22.

As shown in FIG. 7, the first grasping member 21 is fixed to the distal-end side of the cap 1 to not be rotatable. The first grasping member 21 is fixed to the cap 1 at the lower side B2 with respect to the central axis O of the cap 1. As shown in FIG. 3, the first grasping member 21 is arranged at a position overlapping the second penetration hole 12 in the front view. On the other hand, as shown in FIG. 8, the first grasping member 21 is arranged at the position not to overlap the objective lens 215 and the forceps port 214 of the endoscope 200 in the front view.

As shown in FIG. 8, the second grasping member 22 includes the visual-field space 25 penetrating in the open-close direction R between the staple reception portion 4 at the distal-end side and the open-close rotation shaft 23 at the proximal-end side. In the present embodiment, the visual-field space 25 is the space being surrounded by the sides of the U-shaped member 22a formed in the substantially U-shape. In other words, in the front view shown in FIG. 8, when the grasping portion 2 enters the open state, the objective lens 215 and the forceps port 214 of the endoscope 200 are exposed to the visual-field space 25 formed in the U-shaped member 22a of the second grasping member 22 described below.

In the present embodiment, the position of the open-close rotation shaft 23 in the front view shown in FIG. 8, the position of the objective lens 215 provided in the endoscope 200 connected with the cap 1, and the position of the forceps insertion port 222 formed in the endoscope 200 satisfy a predetermined positional relationship. As shown in FIG. 8, a distance (first distance) between the central axis O4 of the endoscope 200 and the open-close rotation shaft 23 in the up-down direction B is defined as the distance $L_S$, a distance (second distance) between the central axis O4 of the endoscope 200 and the central axis of the objective lens 215 is defined as the distance $L_{CL}$, and a radius of a circle with the central axis O4 of the endoscope 200 as the center that circumscribes the forceps insertion port 222 is defined as the radius $R_F$. In the present embodiment, the distance $L_S$ between the central axis O4 of the endoscope 200 and the open-close rotation shaft 23 is equal to or larger than the radius $R_F$. The distance $L_S$ between the central axis O4 of the endoscope 200 and the open-close rotation shaft 23 is equal to or larger than the distance $L_{CL}$ between the central axis O4 of the endoscope 200 and the central axis of the objective lens 215.

According to the present embodiment, the distance $L_S$ between the central axis O4 of the endoscope 200 and the open-close rotation shaft 23 is equal to or larger than the radius $R_F$ such that it is possible to avoid the interference between the grasping portion 2 and various endoscopic treatment devices inserted through the forceps insertion port 222 including the grasping forceps G described below. In other words, with respect to the grasping portion 2 in the open state or the closed state, it is possible to advance and retract the endoscopic treatment devices inserted through the forceps insertion port 222 to perform the treatment with respect to the treatment target T.

According to the present embodiment, the distance $L_S$ between the central axis O4 of the endoscope 200 and the open-close rotation shaft 23 is equal to or larger than the distance $L_{CL}$ between the central axis O4 of the endoscope 200 and the central axis of the objective lens 215 such that when the various endoscopic treatment devices are inserted through the forceps insertion port 222 to be operated to advance and retract, it is possible to prevent the visual field of the objective lens 215 for observing the treatment target T from being cut off.

Figures 9, 10:
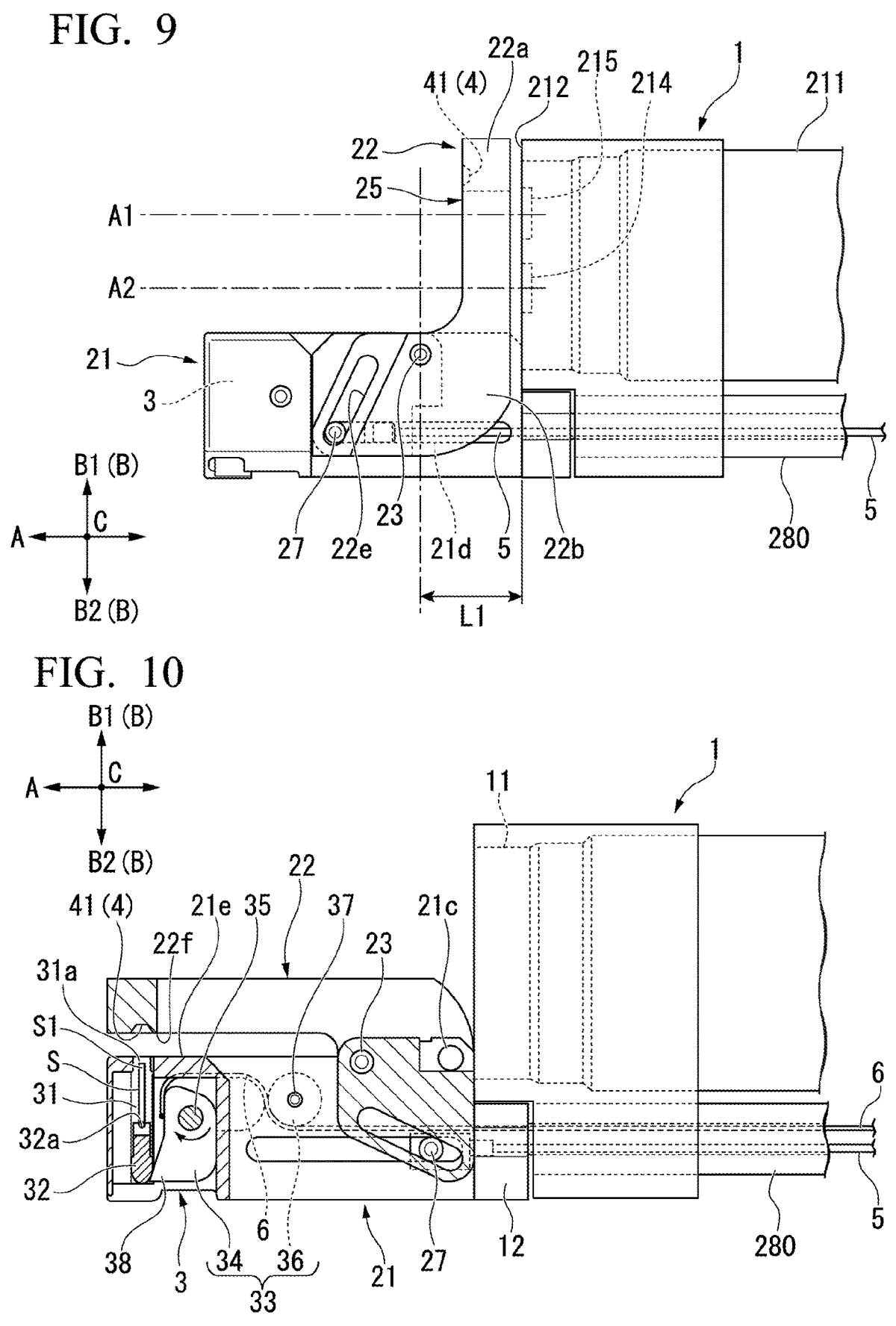

As shown in FIG. 6, the movable pin 27 is engaged in the first engagement groove 21d and the second engagement groove 22e, and is movable in the axial direction A along the first engagement groove 21d. The distal end of the open-close operation wire 5 is attached to the movable pin 27. As shown in FIG. 9, when the movable pin 27 advances toward the distal-end side together with the open-close operation wire 5 by the operations of the surgeon, the second grasping member 22 rotates with respect to the first grasping member 21 with the open-close rotation shaft 23 as the center such that the grasping portion 2 enters the open state. At this time, the first grasping member 21 and the second grasping member 22 form an angle of substantially 90 degrees. That is, the first grasping member 21 and the second grasping member 22 are substantially orthogonal to each other. On the other hand, when the movable pin 27 retracts to the proximal-end side together with the open-close operation wire by the operations of the surgeon, as shown in FIG. 6, the second grasping member 22 rotates with respect to the first grasping member 21 with the open-close rotation shaft 23 as the center such that the grasping portion 2 enters the closed state. As shown in FIG. 6 and FIG. 9, when the movable pin 27 advances from the position at the proximal-end side than the open-close rotation shaft 23 to the distal-end side of the endoscope 200 along the axial direction A, the grasping portion 2 transitions from the closed state to the open state. On the other hand, when the movable pin 27 retracts from the position at the distal-end side than the open-close rotation shaft 23 to the proximal-end side of the endoscope 200, the grasping portion 2 transitions from the open state to the closed state. It is preferable that the movable pin 27 is aligned with the surfaces of the first grasping member 21 and the second grasping member 22 in the axial direction C or slightly pop out from the surfaces of the first grasping member 21 and the second grasping member 22 in the axial direction C.

As shown in FIG. 9, when the grasping member 2 is in the open state, the staple reception portion 4 is disposed at the proximal-end side than the open-close rotation shaft 23. As shown in FIG. 6, FIG. 7, and FIG. 9, when the grasping portion 2 is in the open state, the staple extraction portion 3 and the staple reception portion 4 are arranged at two sides of the optical axis A1 of the objective lens 215 to sandwich the optical axis A1 of the objective lens 215. When the grasping portion 2 is in the open state, the optical axis A1 of the objective lens 215 passes through the visual-field space 25. Also, when the grasping portion 2 is in the open state, the central axis A2 of the forceps port 214 passes through the visual-field space 25.

FIG. 10 is a cross-sectional view showing the grasping portion 2 including the staple extraction portion 3.

The staple extraction portion 2 is arranged in the first distal-end portion 21a of the first grasping member 21 and configured to accommodate and extract the staples S. The staple extraction portion 3 includes a staple accommodation portion 31, a straight-moving member 32, and a rotation member 33.

The staple accommodation portion 31 is the space provided in the first distal-end portion 21a of the first grasping member 21 for accommodating the staples S. As shown in FIG. 7, two of the staple accommodation portions 31 are formed side by side in the axial direction C in the first grasping member 21 so as to be able to accommodate two of the U-shaped staples S.

The staple accommodation portion 31 has the opening 31a provided on the upper surface 21e of the first distal-end portion 21a to open in the up-down direction B. The staples S are accommodated in the staple accommodation portion 31 from the opening 31a. The staples S are accommodated in the staple accommodation portion 31 in the state in which the needle tip S1 of the staple S is directed toward the upper side B1.

In the planar view, the staple accommodation portion 31 is formed in a rectangular shape that the short side extends in the axial direction A and the long side extends in the axial direction C. The staples S accommodated in the staple accommodation portion 31 are arranged that the needle tips S1 at two ends thereof are arrayed in the axial direction C.

The straight-moving member 32 is the member accommodated in the staple accommodation portion 31 and movable in the inside space of the staple accommodation portion 31 along the up-down direction B. The straight-moving member 32 includes the concave portion 32a at the upper side B1 to support the staple S. The staple S accommodated in the staple accommodation portion 31 is fitted into the concave portion 32a.

A first pulley 34 and a second pulley 36 as the rotation member 33 are attached to the inside of the first grasping member 21 to be rotatable, and the first pulley 34 and the second pulley 36 rotate so as to move the straight-moving member 32 in the up-down direction B. The distal-end of the extraction operation wire 6 is connected to the first pulley 34. It is possible to rotate the first pulley 34 by pulling the extraction operation wire 6.

The second pulley 36 is attached to the inside of the first grasping member 21 to be rotatable, and the first pulley 34 is disposed at the distal-end side of the second pulley 35. The rotation axis 35 of the first pulley 34 and the rotation axis 37 of the second pulley 36 extend in the axial direction C and substantially parallel to the open-close shaft 23 of the grasping portion 2. The first pulley 34 includes the convex portion (contact portion) 38 at the distal-end side to support the straight-moving member 32 from the lower side B2.

The distal end of the extraction operation wire 6 is connected to the first pulley 34 at the position at the upper side B1 than the rotation axis 35. The extraction operation wire 6 passes through the second penetration hole 12 from the first pulley 34 via the second pulley 36 to extend to the extraction operation portion 270. The reason for providing the second pulley 36 is to suitably perform the position adjustment for guiding the extraction operation wire 6 to the second penetration hole 12 and reduce the friction resistance at the time of guiding the extraction operation wire 6 to the second penetration hole 12. Accordingly, the same effect can be achieved by using the first pulley 34 only as the rotation member 33 and providing a member (friction-reduction member) in an R-shape and with a suitable slidability instead of the second pulley 36.

Figure 11:
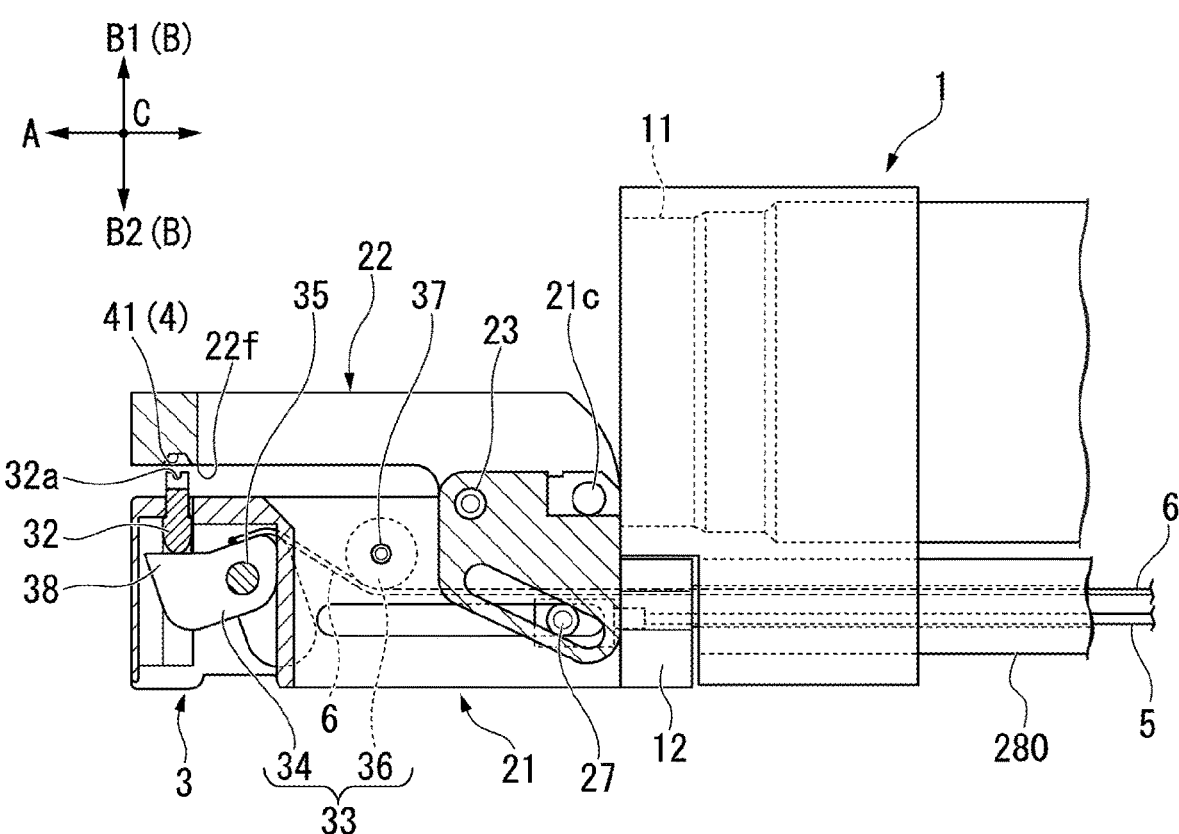
FIG. 11 is a cross-sectional view showing the grasping portion in which an extraction operation wire is pulled.

FIG. 11 is a cross-sectional view showing the grasping portion 2 in which the extraction operation wire 6 is pulled.

By pulling the extraction operation wire 6, the portion at the upper-side B1 of the first pulley 34 rotates to the proximal-end side, and the portion at the lower-side B2 of the first pulley 34 rotates to the distal-end side. As a result, the convex portion 38 of the first pulley 34 pushes up the straight-moving member 32 to the upper-side B1 to extract the accommodated staple S to the upper-side b1 from the opening 31a.

The staple reception portion 4 is provided on the lower surface 22f of the second distal-end portion 22c of the second grasping member 22. The staple reception portion 4 is provided with a plurality of pockets 41 being capable of accommodating the staples extracted from the staple extraction portion 3. In the present embodiment, two of the U-shaped staples are extracted from the staple extraction portion 3 such that there are four pockets 41 are provided in the staple reception portion 4. As shown in FIG. 10, when the grasping portion 2 is in the closed state, the opening 31a from which the staple S is extracted and the pocket 41 of the staple extraction portion 3 are opposite to each other.

As shown in FIG. 10 and FIG. 11, in the medical stapler 100 according to the present embodiment, the extraction operation wire 6 is disposed to be closer to the open-close rotation shaft 23 side than the open-close operation wire 5. In other words, in the medical stapler 100, the extraction operation wire 6 is positioned at the upper side of the cap 1 than the open-close operation wire 5. The medical stapler 100 has such a configuration such that the staple accommodation portion 31, the straight-moving member 32, and the rotation member 33 included in the staple extraction portion

3 can be arranged to avoid the movable range of the movable pin 27, that is, the range in which the first engagement groove 21d is formed. In other words, the open-close operation wire 5 and the extraction operation wire 6 are arranged in this configuration such that the staple accommodation portion 31, the straight-moving member 32, and the rotation member 33 are arranged at the lower side B2 of the medical stapler 100 or at the distal-end side in the axial direction A so as to avoid the upsizing of the staple extraction portion 3.

[Operations of Medical Stapler 100]

Next, the operations of the medical stapler 100 will be described. FIG. 12 to FIG. 15 are views for describing the operations of the medical stapler 100.

Figure 12:
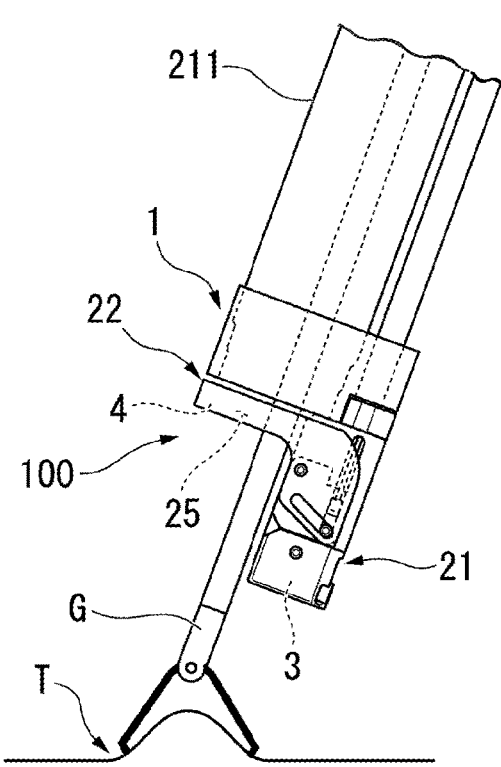
FIG. 12 is a view describing operations of the medical stapler.

The surgeon moves the distal-end portion 211 of the endoscope 200 to which the medical stapler 100 is attached to approach the treatment target T. The surgeon operates the open-close operation portion 250 to advance the open-close operation wire 5 to make the grasping portion 2 into the open state. The optical axis A1 of the objective lens 215 passes through the visual-field space 25 such that the surgeon can observe the treatment target T through the imaging unit of the endoscope 200. Also, the central axis A2 of the forceps port 214 passes through the visual-field space 25 such that as shown in FIG. 12, the surgeon can protrude the grasping forceps G from the forceps port 214 to perform the treatment with respect to the treatment target T.

Figure 13:
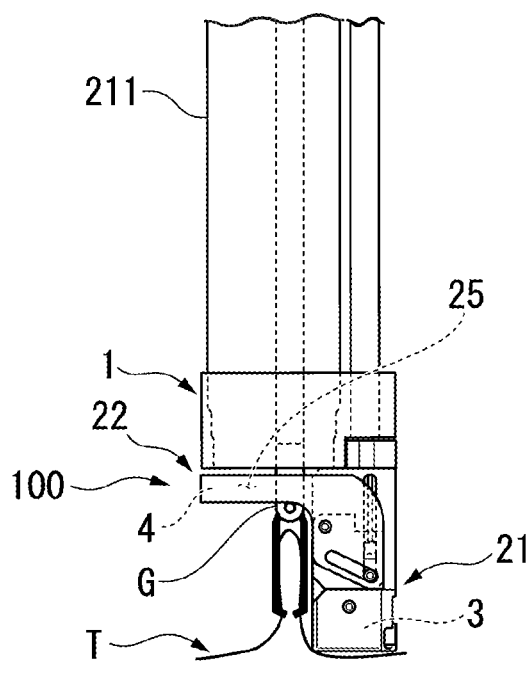
FIG. 13 is a view describing the operations of the medical stapler.

As shown in FIG. 13, the surgeon retracts the grasping forceps C in the state of grasping the treatment target T by the grasping forceps G. The surgeon retracts the grasping forceps G so as to dispose the distal end of the grasping forceps G at the proximal-end side than the staple extraction portion 3.

Figure 14:
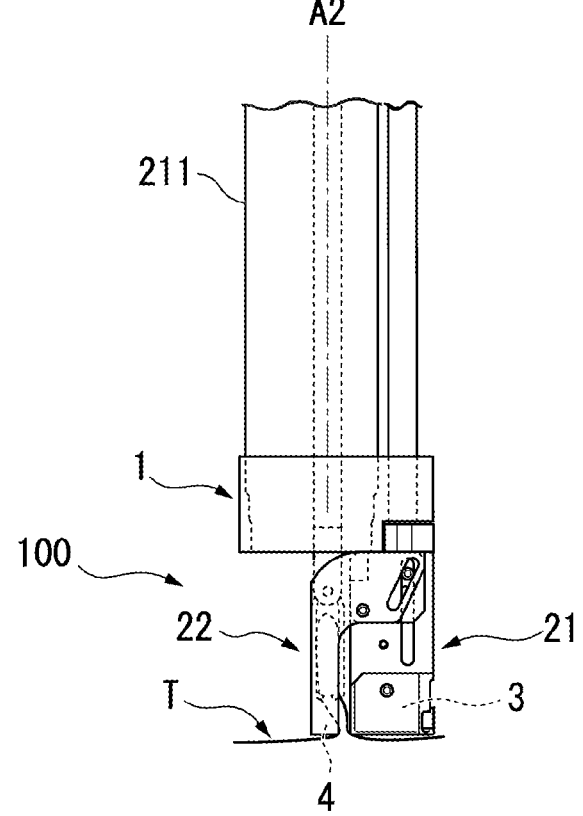
FIG. 14 is a view describing the operations of the medical stapler.

As shown in FIG. 14, the surgeon operates the open-close operation portion 250 to retract the open-close operation wire 5 to cause the grasping portion 2 in the closed state. The treatment target T is clamped by the staple extraction portion 3 of the first grasping member 21 and the staple reception portion 4 of the second grasping member 22.

When the grasping portion 2 is in the closed state, part of the treatment target T that is clamped by the grasping forceps G can be accommodated in the space (visual-field space 25) formed by the U-shaped member 22a and the second main body portion 22b of the second grasping member 22 such that it is difficult for the treatment target T that is clamped by the staple extraction portion 3 and the staple reception portion 4 to escape.

As shown in FIG. 8, when the grasping portion 2 is in the closed state, the optical axis A1 of the objective lens 215 passes through the outside of the first grasping member 21 and the second grasping member 22. Accordingly, it is also possible for the surgeon to observe the treatment target T through the imaging unit of the endoscope 200 even when the grasping portion 2 is in the closed state.

The surgeon operates the extraction operation portion 270 to pull the extraction operation wire 6 in the state in which the treatment target T is clamped by the staple extraction portion 3 and the staple reception portion 4 to extract the accommodated staples S toward the staple reception portion 4. The needle tips S1 of the staple S penetrate the treatment target T to come into contact with the pocket 41 of the staple reception portion 4 to be bent. As a result, the treatment target T is sutured.

Figure 15:
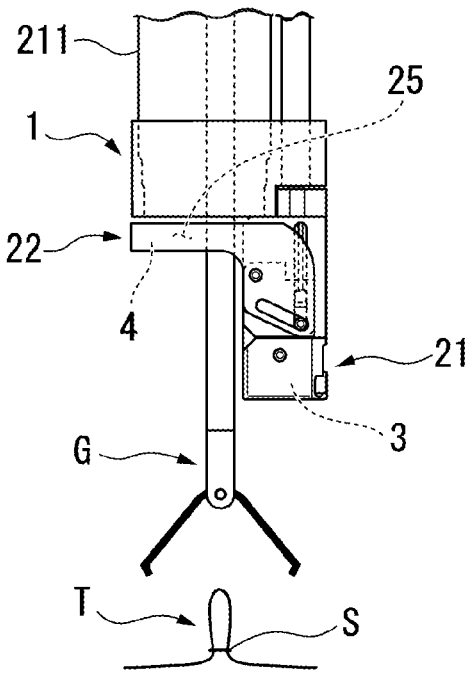
FIG. 15 is a view describing the operations of the medical stapler.

As shown in FIG. 15, the surgeon operates the open-close operation portion 250 to make the grasping portion 2 into the open state again. The surgeon separates the grasping forceps G from the treatment target T to finish the suturing treatment.

According to the medical stapler 100 disclosed in the present embodiment, the insertion diameter of the medical stapler 100 in which the grasping portion 2 is in the closed state is substantially the same with that of the distal-end portion 211 of the endoscope 200 such that it is easy to be inserted into the body such as the gastrointestinal tract or the like. Also, even the grasping portion 2 of the medical stapler 100 is in the open state, the surgeon can observe the treatment target T via the imaging unit of the endoscope 200 and protrude the grasping forceps C from the forceps port 214 to perform the treatment with respect to the treatment target T.

According to the medical stapler 100 disclosed in the present embodiment, the open-close rotation shaft 23 is disposed at the distal-end side of the distal end 212 of the endoscope 200. According to the configuration, the outer diameter in the radial direction of the medical stapler 100 is formed to be thinner as compared with the stapler configured to cover the endoscope that is disclosed in the conventional technology. As a result, even in a narrow surgery site such as the gastrointestinal tract or the like in the body of the patient, it is possible to smoothly switch the open state and the closed state of the grasping portion 2 of the medical stapler 100.

According to the medical stapler 100 disclosed in the present embodiment, the position of the open-close rotation shaft 23, the position of the objective lens 215 provided in the endoscope 200, and the position of the forceps insertion port 222 satisfy the predetermined positional relationship. Accordingly, the opening operation and the closing operation of the grasping portion 2 of the medical stapler 100 and the operations to introduce the endoscopic treatment device via the forceps insertion port 222 do not interfere with each other. It is possible to prevent the visual field of the objective lens 215 of the endoscope 200 from being cut off by the opening operation and the closing operation of the grasping portion 2 of the medical stapler 100.

According to the medical stapler 100 disclosed in the present embodiment, the extraction operation wire 6 is disposed to be closer to the open-close rotation shaft 23 side than the open-close operation wire 5. Accordingly, it is possible to realize the miniaturization of the medical stapler 100.

According to the medical stapler 100 disclosed in the present embodiment, when the grasping portion 2 is in the open state, the second grasping member 22 is positioned between the open-close rotation shaft 23 and the endoscope 200 in the axial direction A. Accordingly, it is possible to prevent the second grasping member 22 from entering the visual field of the objective lens 215 provided in the endoscope 200.

According to the medical stapler 100 disclosed in the present embodiment, the movable pin 27 advances and retracts in the state of engaging with the first engagement groove 21d together with the advancement and the retraction of the open-close operation wire 5. Accordingly, it is possible for the surgeon to operate the open-close operation wire 5 with a relatively small force so as to make the grasping portion 2 to transition to the open state and the closed state. The movable pin 27 is provided to be freely advanceable and retractable along the longitudinal direction of the endoscope 200 between the position at the proximal-end side of the open-close rotation shaft 23 and the positon at the distal-end side of the open-close rotation shaft 23 in the state of engaging with the first engagement groove 21d of the first grasping member 21. According to the configuration, the medical stapler 100 according to the present embodiment is formed as the small mechanism and when the grasping portion 2 is in the open state, the opening angle between the first grasping member 21 and the second grasping member 22 is large.

As described above, the first embodiment of the present disclosure has been described in detail with reference to the drawings, however, the specific configuration is not limited to the present embodiment, and design changes and the like are included within the scope of the present invention. Also, the configuration elements shown in the above-described embodiment and modification examples can be combined as appropriate.

Second Embodiment

Figure 17:
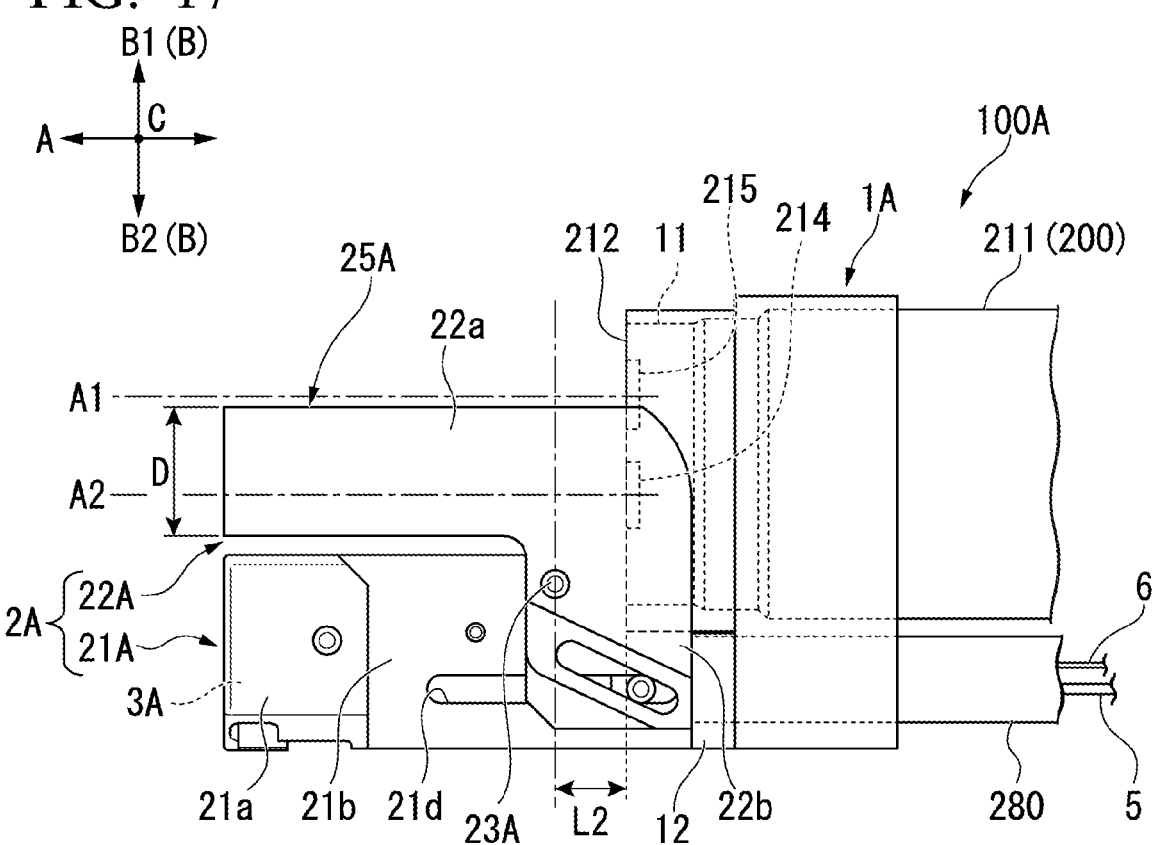
FIG. 17 is a side view in which a grasping portion of the medical stapler according to the present embodiment is in a closed state.
Figure 18:
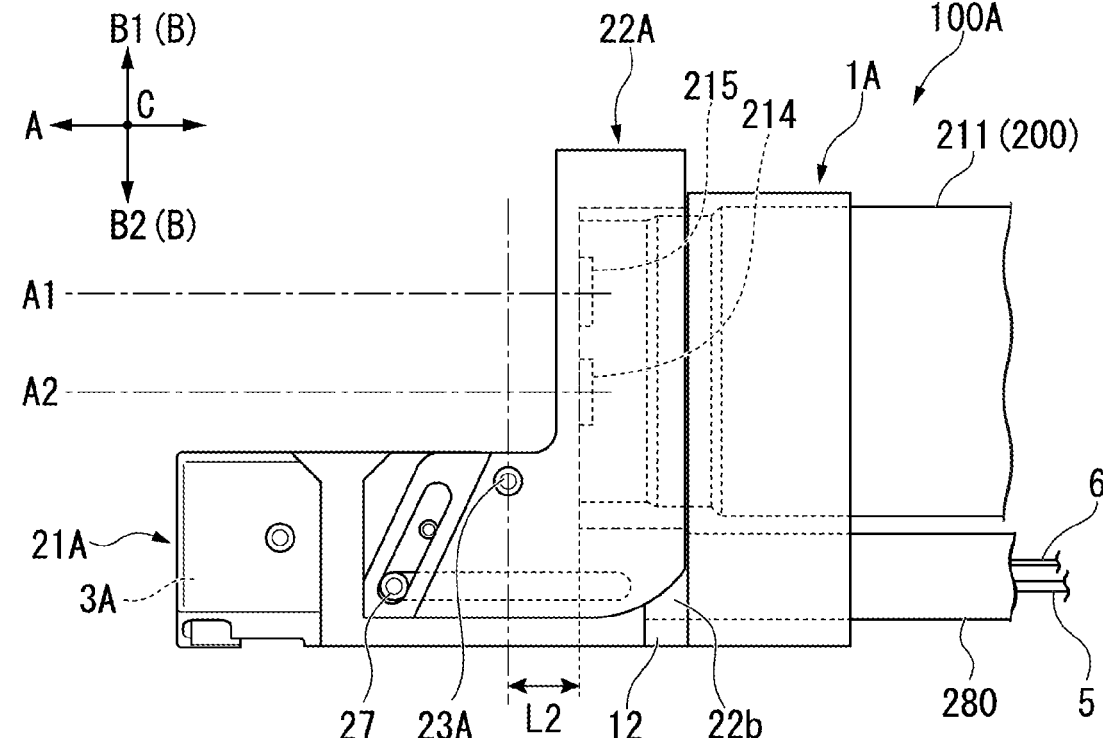
FIG. 18 is a side view in which the grasping portion of the medical stapler according to the present embodiment is in an open state.

Hereinafter, a medical stapler 100A according to a second embodiment of the present disclosure will be described by referring to FIG. 16 to FIG. 18. In the following description, the common configuration that have been described will be designated with the same reference signs and the duplicate description will be omitted.

Figure 16:
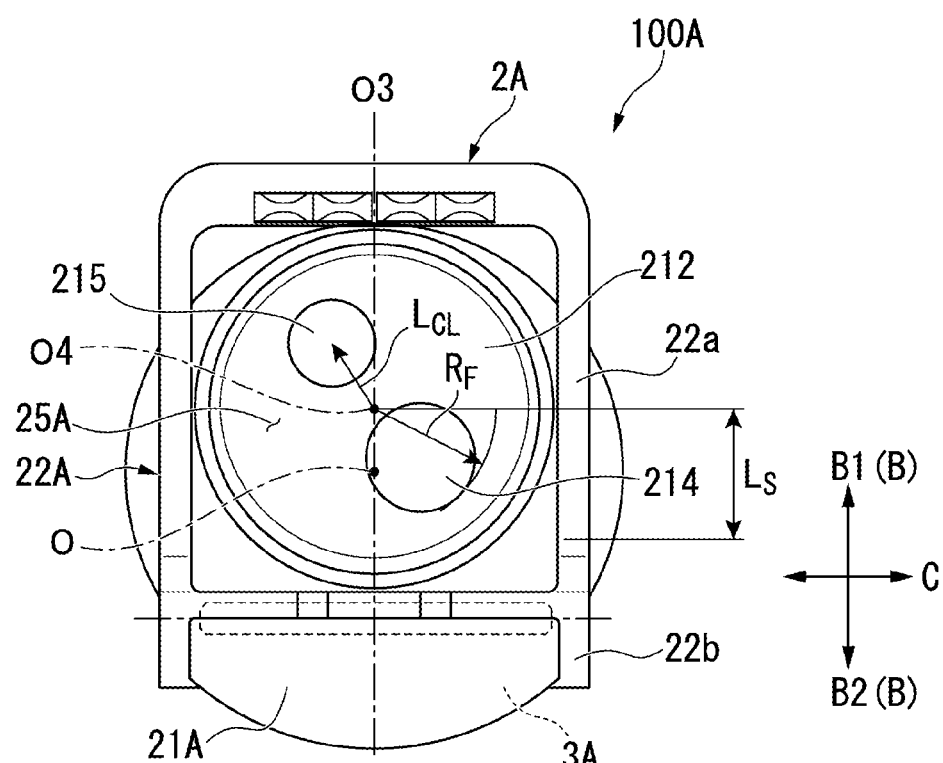
FIG. 16 is a front view showing a medical stapler according to a second embodiment of the present disclosure.

FIG. 16 is a front view showing a grasping portion 2A of the medical stapler 100A in the open state according to the present embodiment. FIG. 17 is a side view showing the grasping portion 2A in the closed state. FIG. 18 is a side view showing the grasping portion 2A in the open state.

As shown in FIG. 16, as compared with the grasping portion 2 of the medical stapler 100 according to the first embodiment, the grasping portion 2A of the medical stapler 100A in the open state according to the present embodiment includes a second grasping member 22A in which a larger visual-field space 25A is formed therein. As shown in FIG. 17, in the medial stapler 100A according to the present embodiment, a thickness D in the up-down direction B of the second grasping member 22A in the closed state is larger than the thickness of the second grasping member 22 of the medical stapler 100 according to the first embodiment. As shown in FIG. 17, the distance L2 between the open-close rotation shaft 23A of the medical stapler 100A and the distal end 212 of the endoscope 200 is smaller than the distance L1 in the medical stapler 100 according to the first embodiment.

According to the present embodiment, when the grasping portion 2A is in the open state, the outer diameter of the distal-end portion of the cap 1A is smaller than that according to the first embodiment such that the second grasping member 22A does not collide with the cap 1A. The medical stapler 100A according to the present embodiment has the above-described configuration such that when the grasping portion 2A enters the open state, as shown in FIG. 16, the second grasping member 22A of the grasping portion 2A in the open state is positioned at the outside in the radial direction with respect to the endoscope 200 in the front view. Also, as shown in FIG. 18, the second grasping member 22A is arranged to overlap part of the distal-end portion 211 of the endoscope 200 and the cap 1A.

The other configurations of the medical stapler 100A according to the present embodiment are the same with that of the medical stapler 100 according to the above-described first embodiment. For example, as shown in FIG. 17 and FIG. 18, the open-close rotation shaft 23A is positioned at the distal-end side of the distal end 212 of the endoscope 200. For example, in the front view shown in FIG. 16, the position of the open-close rotation shaft 23A, the position of the objective lens 215 provided in the endoscope 200 connected with the cap 1, and the positon of the forceps insertion port 222 formed in the endoscope 200 satisfy the predetermined positional relationship disclosed in the first embodiment.

According to the medical stapler 100A disclosed in the present embodiment, when the grasping portion 2A enters the open state, the second grasping member 22A is positioned at the outside in the radial direction than the endoscope 200 such that the outer diameter thereof is larger than that of the medical stapler 100 according to the first embodiment. However, compared with the configuration disclosed in the conventional technology, the insertion diameter of the medical stapler 100A is sufficiently small. Accordingly, according to the medical stapler 100A disclosed in the present embodiment, similar to the medical stapler 100 according to the first embodiment, it is possible to perform the treatment on the treatment target T even in the narrow surgery site by transitioning the grasping portion 2 to the open state and the closed state. According to the medical stapler 100A disclosed in the present embodiment, it is possible to realize the treatment with respect to the treatment target T by using a thicker second grasping member and the treatment with respect to the treatment target T by using the medical stapler having a shorter length in the axial direction A.

Third Embodiment

Hereinafter, a medical stapler 100B according to a third embodiment of the present disclosure will be described by referring to FIG. 19 to FIG. 21. The medical stapler 100B according to the present embodiment is different from the medical stapler 100 according to the above-described first embodiment in the opening direction of the grasping portion in the open state.

Figure 19:
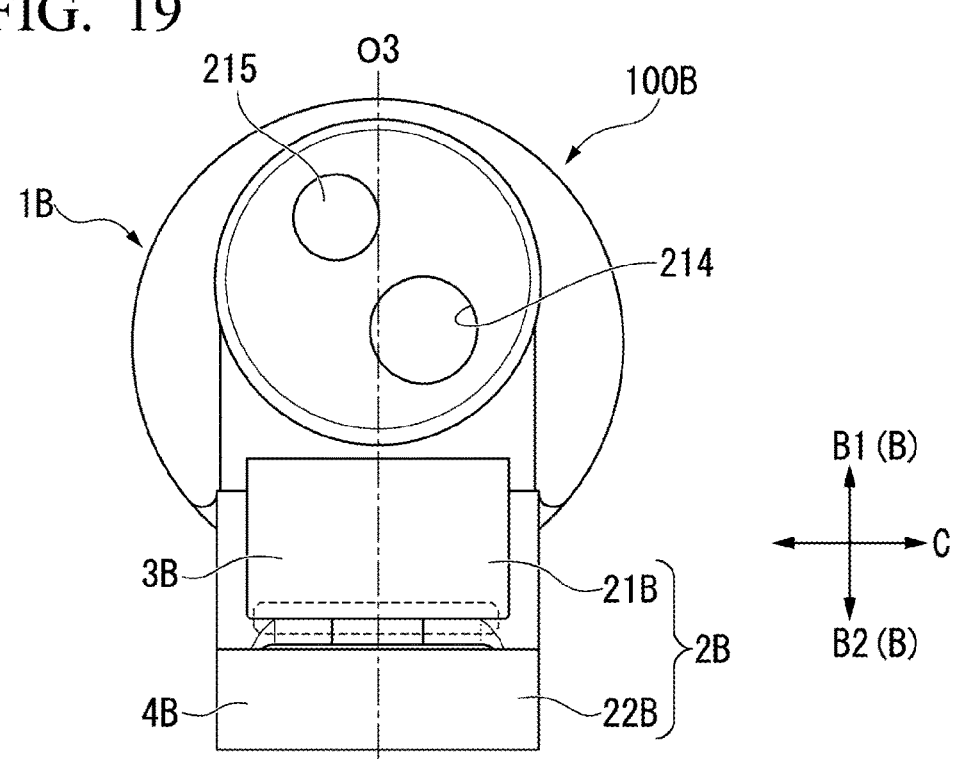
FIG. 19 is a front view showing a cap of a medical stapler according to a third embodiment of the present disclosure.
Figure 20:
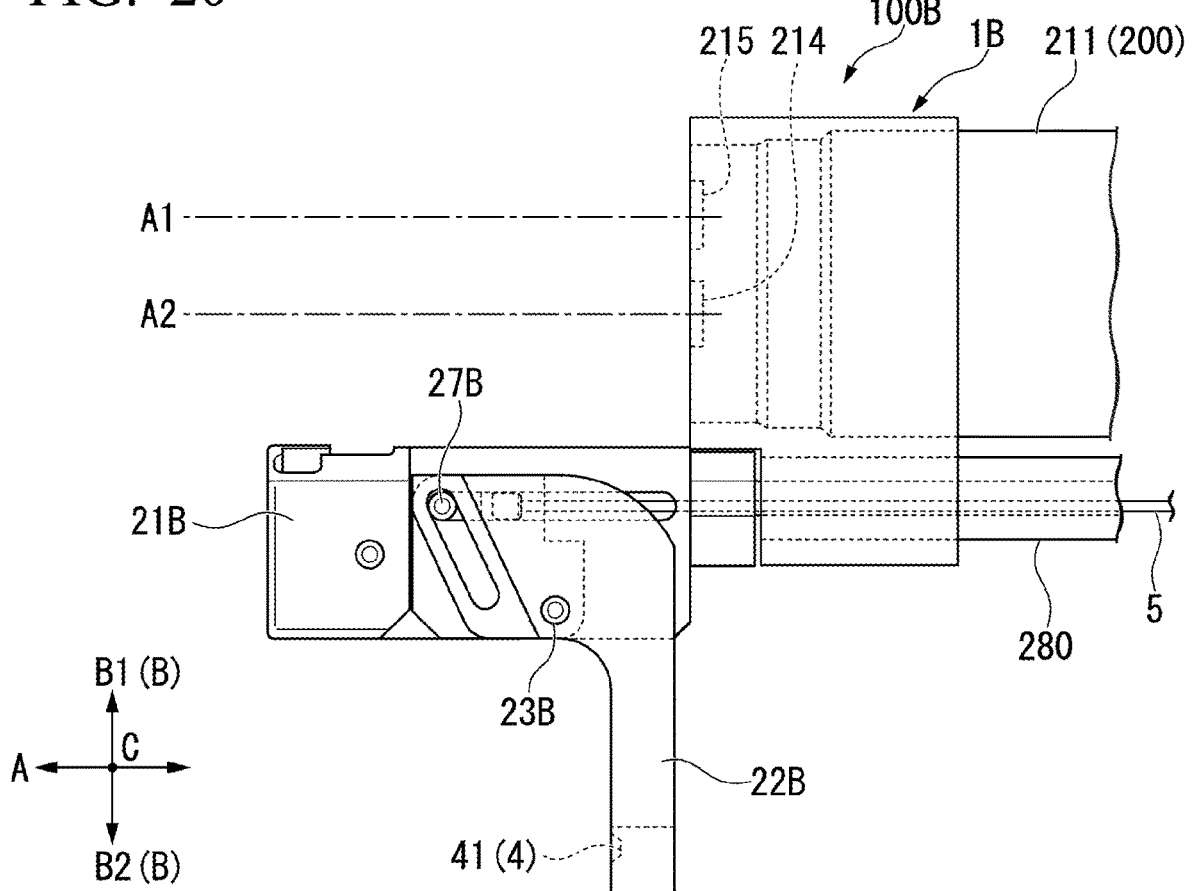
FIG. 20 is a side view in which a grasping portion of the medical stapler according to the present embodiment is in an open state.

FIG. 19 is a front view when the grasping portion 2B of the medical stapler 100B according to the present embodiment is in the closed state. FIG. 20 is a side view when the grasping portion 2B of the medical stapler 100B according to the present embodiment is in the open state. FIG. 21 is a view for describing the operation of the treatment using the medical stapler 100B.

As shown in FIG. 19, in the medical stapler 100B according to the present embodiment, the second grasping member 22B of the grasping portion 2B is arranged at the outside than the first grasping member 21B in the radial direction of the medical stapler 100B. As shown in FIG. 20, with respect to the medical stapler 100B, when the surgeon presses the open-close operation wire 5, the second grasping member 22B rotates with respect to the first grasping member 21B such that the grasping portion enters the open state. At this time, the grasping portion 2B in the open state opens toward the lower side B2 of the endoscope 200. The other configurations of the medical stapler 100B according to the present embodiment are the same with that of the medical stapler 100 according to the above-described medical stapler 100.

Figure 21:
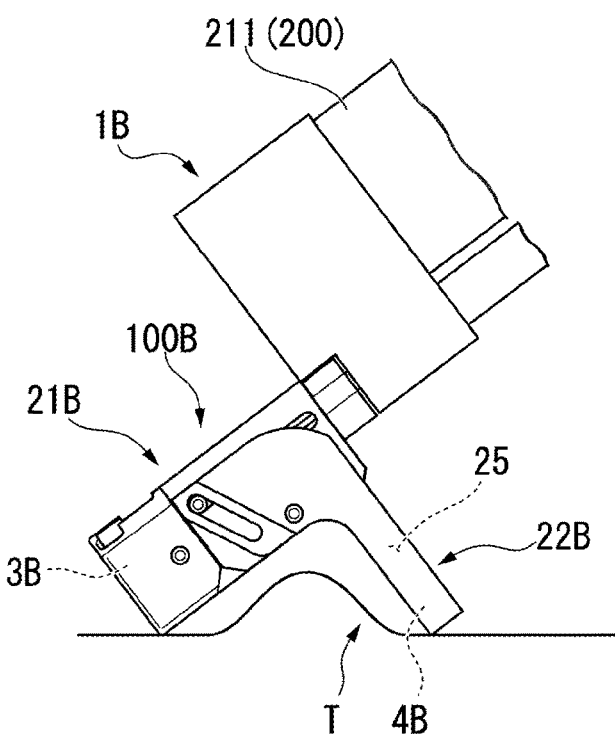
FIG. 21 is a view describing operations of the medical stapler according to the present embodiment.

As shown in FIG. 21, at the time of using the medical stapler 100B according to the present embodiment to perform the treatment with respect to the treatment target T, the visual field of the objective lens 215 of the endoscope 200 is cut off by the grasping portion 2B. That is, it is impossible for the surgeon to acquire the images or the like of the treatment target T by using the objective lens 215 of the endoscope 200. However, in a case in which the dimension of the treatment target T is small, it is possible for the surgeon to directly transition the grasping portion 2B to the closed state to perform the treatment with respect to the treatment target T without confirming the images of the treatment target T.

According to the medical stapler 100B disclosed in the present embodiment, in the case in which the dimension of the treatment target T is small, it is possible for the surgeon to directly perform the treatment with respect to the treatment target T without confirming the images acquired by the objective lens 215 of the endoscope 200. In this case, it is unnecessary for the surgeon to operate the objective lens 215 of the endoscope 200 and the endoscopic treatment device such that the surgery becomes simple.

Fourth Embodiment

Hereinafter, a medical stapler 100C according to a fourth embodiment of the present disclosure will be described by referring from FIG. 22 to FIG. 24. The medical stapler 100C according to the present embodiment is different from the medical stapler 100 according to the above-described first embodiment in the shape of the second grasping member 22C.

Figure 22:
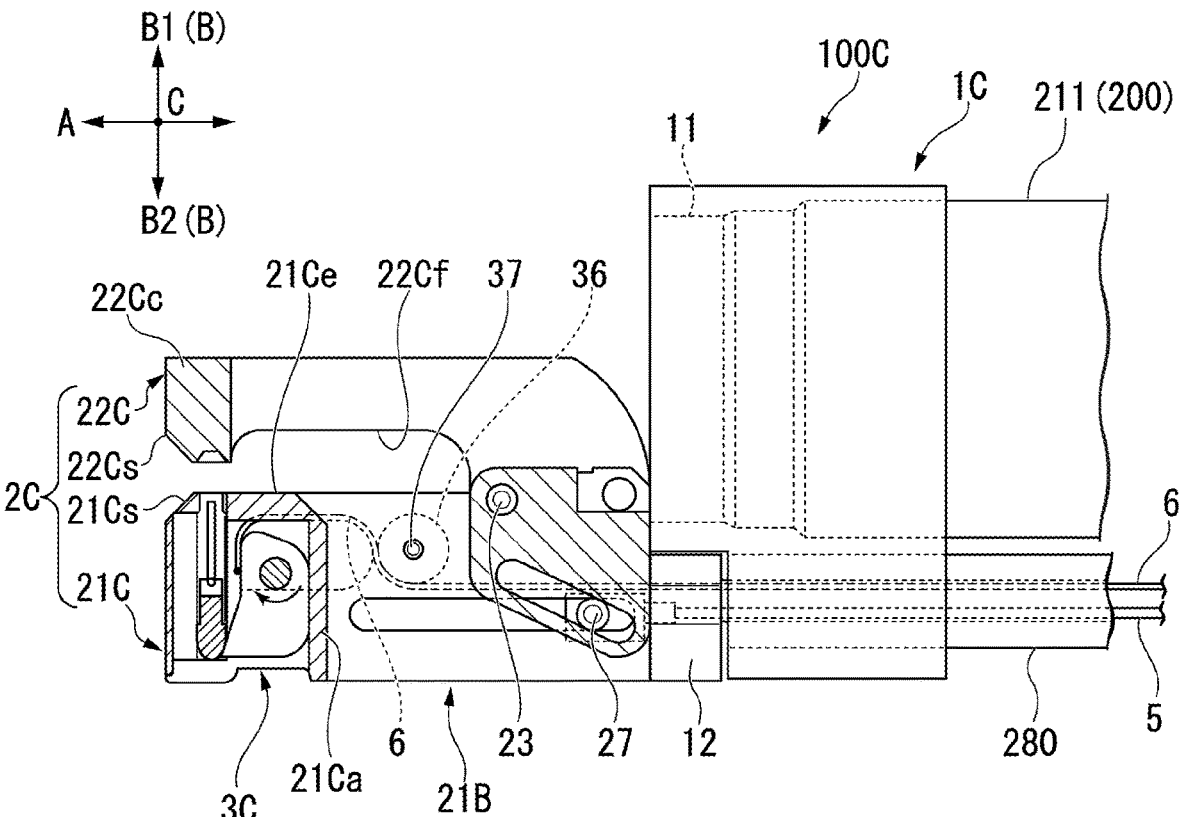
FIG. 22 is a cross-sectional view showing a grasping portion of a medical stapler according to a fourth embodiment of the present disclosure.

FIG. 22 is a cross-sectional view showing a grasping portion 2C of the medical stapler 100C in the closed state according to the present embodiment. FIG. 23 is a side view showing the grasping portion 2C of the medical stapler 100C in the closed state. FIG. 24 is a partial enlarged view showing the grasping portion 2C of the medical stapler 100C in the closed state.

Figure 23:
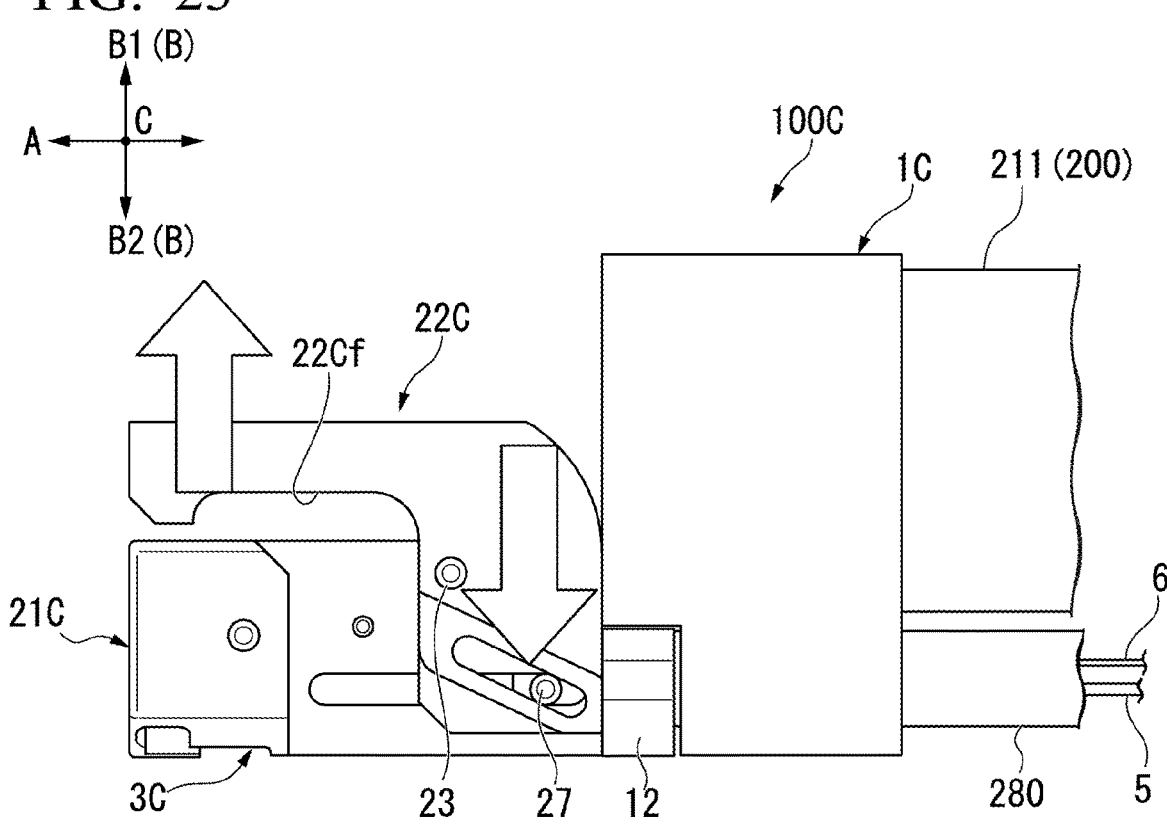
FIG. 23 is a side view in which the grasping portion of the medical stapler according to the present embodiment is in a closed state.

As shown in FIG. 22 and FIG. 23, the grasping portion 2C includes the first grasping member 21C, the second grasping member 22C, the open-close rotation shaft 23, and the movable pin 27. The first grasping member 21C and the second grasping member 22C are connected by the open-close rotation shaft 23 to be openable and closeable.

Compared with the first grasping member 21 according to the first embodiment, the first grasping member 21C is different in the shape of a first distal-end portion 21Ca. A first inclination surface 21Cs inclined with respect to the central axis O is provided at the distal-end side on the upper surface 21Ce of the first distal-end portion 21Ca included in the first grasping member 21C.

Compared with the second grasping member 22 according to the first embodiment, the second grasping member 22C is different in the shape of the second distal-end portion 22Cc and the U-shaped member 22Ca. A second inclination surface 22Cs inclined with the central axis O at the distal-end side is formed in the lower surface 22Ce of the second distal-end portion 22Cc included in the second grasping member 22C. The U-shaped member 22Ca included in the second grasping member 22C included a concave portion 22Cf at the inside being opposite to the first grasping member 21C when the grasping portion 2C is in the closed state. The concave portion 22Cf is recessed toward the outside being opposite to the inside from the inside thereof.

As shown in FIG. 22, when the grasping portion 2C is in the closed state, the first inclination surface 21Cs and the second inclination surface 22Cs form a tapered surface Ts widen at the distal-end side. When the surgeon grasps the treatment target T by the grasping portion 2C, the treatment target T is grasped along the tapered surface Ts. Accordingly, the grasping portion 2C is configured to definitely grasp the treatment target T and it is difficult for the treatment target T to escape from the grasping portion 2C.

As shown in FIG. 22, the grasping portion 2C includes the concave portion 22Cf such that when the surgeon grasps the treatment target T using the grasping portion 2C, the space in the grasping portion 2C for accommodating the treatment target T is wide. The treatment target T is hooked on the second distal-end portion 22Cc in which the staple reception portion 4 is provided so as to prevent the treatment target T from slipping out. Accordingly, the grasping portion 2C can further definitely grasp the treatment target T to make it difficult for the treatment target T to escape from the grasping portion 2C.

Hereinafter, the configuration for smoothly performing the treatment with respect to the treatment target T by using the medical stapler 100C according to the present embodiment will be described based on FIG. 23 and FIG. 24. As shown in FIG. 23, in the state in which the treatment target T is grasped by the grasping portion 2C, both the repulsive force by the living tissue as the treatment target T and the force to pull the open-close operation wire 5 to the proximal-end side are applied to the grasping portion 2C. That is, the first grasping member 21C and the second grasping member 22C of the grasping portion 2C grasp the treatment target T to be in a substantially stationary state.

Figure 24:
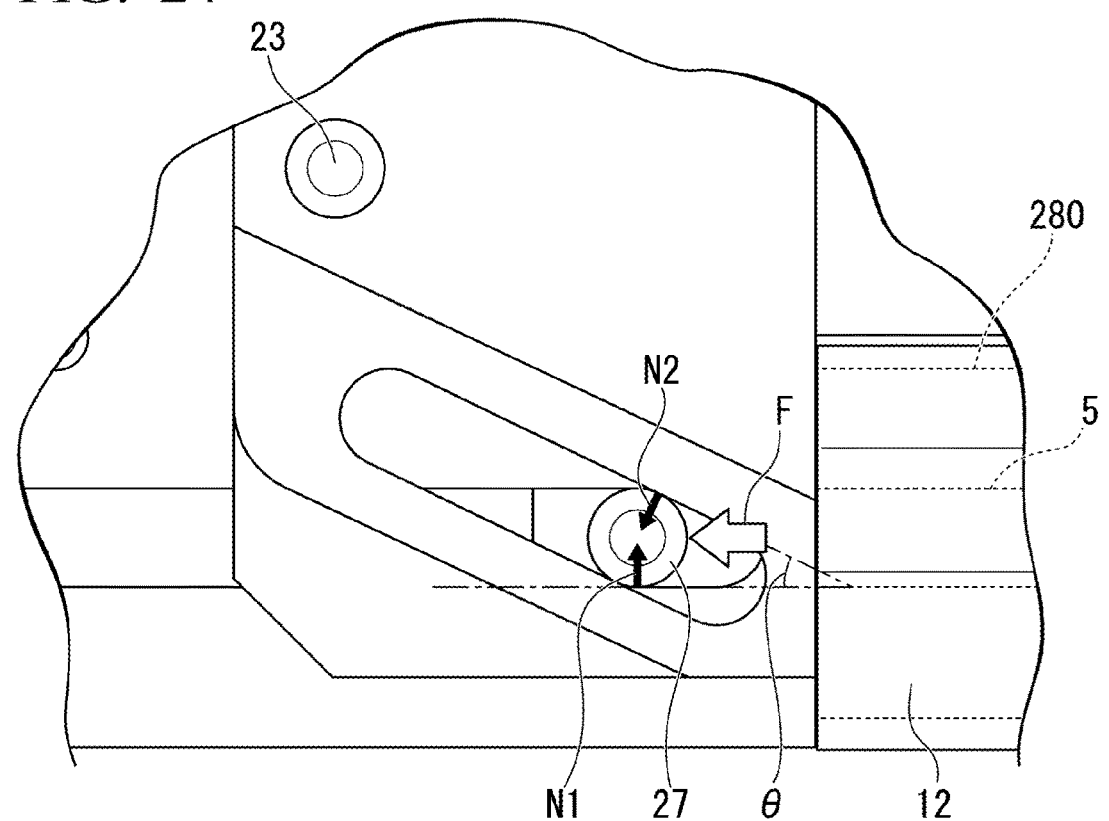
FIG. 24 is a partial enlarged side view showing the grasping portion of the medical stapler according to the present embodiment.

As shown in FIG. 24, an angle formed between the tangent at the contact portion of the first grasping member 21C and the movable pin 27 and the tangent at the contact portion of the second grasping member 22C and the movable pin 27 is defined as a slide angle θ. As shown in FIG. 24, the force N1 due to the repulsive force of the living tissues as the treatment target T and the force N2 due to the force to pull the open-close operation wire 5 are applied on the movable pin 27. At this time, due to the balance of the forces, the force N1 is equal to the component force N2*cos θ of the force N2.

When the treatment with respect to the treatment target T using the medical stapler 100C is performed, for example, by pressing the open-close operation wire 5 to the distal-end side, it is possible to release the treatment target T that is grasped by the grasping portion 2C. On the other hand, for example, at the time of pulling the open-close operation wire 5 while resisting the repulsive force due to the treatment target T, it is necessary to prepare for the case in which the open-close operation wire 5 is broken due to the excessive force applied to the open-close operation wire 5. Accordingly, it is preferable that the grasping portion 2C can be opened only by the repulsive force of the treatment target T even there is no pressing force toward the movable pin 27 by the open-close operation wire 5.

According to the present embodiment, as shown in FIG. 24, due to the operations of pressing the open-close operation wire 5, the open-close operation wire 5 applies the force F to the movable pin 27. Also, the friction coefficient between the first grasping member 21C and the movable pin 27, and the friction coefficient between the second grasping member 22C and the movable pin 27 are the same coefficient μ. Accordingly, the movable pin 27 moves toward the distal-end side in the axial direction A. That is, in order to open the first grasping member 21C and the second grasping member 22C of the grasping portion 2C, it is necessary to satisfy the following equation (1).

$$F + N_2 * \cos\theta > \mu * N_1 + \mu * N_2 + \sin\theta \tag{1}$$

As described above, the value N1 is equal to the value N2*cos θ such that the following equation (2) can be achieved by deforming the above-described equation (1).

$$2 * \mu * N_2 * \cos\theta - N_2 * \sin\theta < F \tag{2}$$

According to the present embodiment, it is preferable that the grasping portion 2C can be opened only by the repulsive force due to the treatment target T, that is, even in the case in which the value F is zero, it is preferable that the grasping portion 2C can be opened, thus the following equation (3) can be achieved.

$$\tan\theta > 2 * \mu \tag{3}$$

That is, by calculating the slide angle θ based on the friction coefficient between the first grasping member 21C and the movable pin 27, and the friction coefficient between the second grasping member 22C and the movable pin 27, it is possible to open the first grasping member 21C and the second grasping member 22C of the grasping portion 2C only by the repulsive force of the treatment target T without operating the open-close operation wire 5. According to the present embodiment, for example, in the case in which the friction coefficient is 0.05, the slide angle may be equal to or larger than 5.7 degrees.

According to the medical stapler 100C disclosed in the present embodiment, similar to the above-described embodiments, even in the narrow surgery site such as the gastro-intestinal tract or the like inside the body of the patient, it is possible to smoothly switch the open state and the closed state of the grasping portion 2C of the medical stapler 100C.

Although the respective embodiments and modifications of the present disclosure have been described above, the technical scope of the present disclosure is not limited to the above-described embodiments, and configurations in the respective embodiments and modifications within the scope not departing from the spirit of the present disclosure. It is possible to change the combination of elements, make various changes to each configuration element, or delete each configuration element. For example, the configuration according to any one of above-described embodiments and modifications of the present disclosure may be appropriately combined with each modification of the operation section. The present disclosure is not limited by the above description, but only by the appended claims.

What is claimed is:

1. A medical stapler, comprising:
a cap configured to attach to an endoscope;
a grasping portion connected to the cap and having a first jaw and a second jaw connected by a rotation shaft;
an operation portion configured to receive an external force for operating the grasping portion to open and close;
a first wire including a proximal end connected with the operation portion and a distal end connected with the grasping portion; and
a movable pin attached to the distal end of the first wire, wherein:
the grasping portion is transitioned to an open state and a closed state by the first jaw and the second jaw relatively rotating around the rotation shaft;
the rotation shaft is positioned more distally than a distal end of the cap; and
the movable pin is advanceable and retractable between a position proximal relative to the rotation shaft and a position distal relative to the rotation shaft in a longitudinal direction of the first jaw in a state in which the movable pin is engaged with an engagement groove formed in the first jaw.

2. The medical stapler according to claim 1, wherein the first jaw and the second jaw are opposite to each other when the grasping portion is in the closed state, and wherein when the grasping portion is in the open state, the first jaw and the second jaw are arranged at 90 degrees to each other.

3. The medical stapler according to claim 1, wherein the first jaw includes a staple extraction portion, wherein the second jaw includes a staple reception portion, and wherein the second jaw rotates with respect to the first jaw around the rotation shaft.

4. The medical stapler according to claim 1, wherein the endoscope includes an objective lens provided in a distal-end portion for observing a treatment target, and wherein a first distance between a central axis of the endoscope and the rotation shaft is equal to or larger than a second distance between the central axis of the endoscope and a center of the objective lens.

5. The medical stapler according to claim 1, wherein the endoscope includes a treatment channel formed to extend from a distal end to a proximal end thereof for inserting an endoscopic treatment device through the endoscope, wherein the treatment channel includes an opening at a distal-end portion of the endoscope, and wherein a first distance between a central axis of the endoscope and the rotation shaft is equal to or larger than a radius of a circle with the central axis of the endoscope as a center that circumscribes the opening.

6. The medical stapler according to claim 1, wherein when the grasping portion is in the open state, the second jaw is positioned between the rotation shaft and the endoscope in the longitudinal direction of the first jaw.

7. The medical stapler according to claim 1, wherein a first region in which the first wire is advanceable and retractable by use of the operation portion is arranged at an outside portion of the rotation shaft in a radial direction of the cap.

8. The medical stapler according to claim 7, further comprising:

a second wire configured to transmit an external force to a staple extraction portion provided in the first jaw so as to extract a staple, wherein a second region in which the second wire is advanceable and retractable by use of the operation portion is arranged at an inside portion of the first region in the radial direction of the cap.

9. The medical stapler according to claim 1, wherein when the grasping portion is in the closed state, a gap having a predetermined distance is formed between a distal-end portion of the first jaw and a distal-end portion of the second jaw.

10. The medical stapler according to claim 1, wherein the first jaw includes a staple extraction portion, wherein the second jaw includes a staple reception portion, wherein the second jaw is provided with a concave portion formed in at least part of a region in a direction from the staple reception portion to the rotation shaft, and wherein a distance between the first jaw to the concave portion is larger than a distance from the first jaw to other part of the second jaw.

11. A medical system, comprising:

an endoscope having flexibility; and a medical stapler engaged with the endoscope, wherein the medical stapler comprises:

a cap configured to attach to the endoscope;

a grasping portion connected to the cap, the grasping portion having a first jaw and a second jaw connected by a rotation shaft;

an operation portion configured to receive an external force for operating the grasping portion to open and close;

a first wire including a proximal end connected with the operation portion and a distal end connected with the grasping portion; and a movable pin attached to the distal end of the first wire, wherein;

the grasping portion is transitioned to an open state and a closed state by the first jaw and the second jaw relatively rotating around the rotation shaft;

the rotation shaft is positioned more distally a distal end of the cap; and the movable pin is advanceable and retractable between a position at a proximal-end side of the rotation shaft and a position at a distal-end side of the rotation shaft in a longitudinal direction of the first jaw in a state in which the movable pin is engaged with an engagement groove formed in the first jaw.

12. The medical system according to claim 11, wherein the first jaw and the second jaw are opposite to each other when the grasping portion is in the closed state, and wherein when the grasping portion is in the open state, the first jaw and the second jaw are arranged at substantially 90 degrees to each other.

13. The medical system according to claim 11, wherein the first jaw includes a staple extraction portion, wherein the second jaw includes a staple reception portion, and wherein the second jaw rotates with respect to the first jaw around the rotation shaft.

14. The medical system according to claim 11, wherein the endoscope includes an objective lens provided in a distal-end portion for observing a treatment target, and wherein a first distance between a central axis of the endoscope and the rotation shaft is equal to or larger than a second distance between the central axis of the endoscope and a center of the objective lens.

15. The medical system according to claim 11, wherein the endoscope includes a treatment channel formed to extend from a distal end to a proximal end thereof for inserting an endoscopic treatment device through the endoscope, wherein the treatment channel includes an opening at a distal-end portion of the endoscope, and wherein a first distance between a central axis of the endoscope and the rotation shaft is equal to or larger than a radius of a circle with the central axis of the endoscope as a center that circumscribes the opening.

16. The medical system according to claim 11, wherein when the grasping portion is in the open state, the second jaw is positioned between the rotation shaft and the endoscope in the longitudinal direction of the first jaw.

17. The medical system according to claim 11, wherein a first region in which the first wire is advanceable and retractable along the longitudinal direction is arranged at an outside portion of the rotation shaft in a radial direction of the cap.

18. The medical system according to claim 17, wherein the medical stapler further comprises:

a second wire configured to transmit an external force to a staple extraction portion provided in the first jaw so as to extract a staple; and a second region in which the second wire is advanceable and retractable along the longitudinal direction is arranged at an inside portion of the first region in the radial direction of the cap.

19. The medical system according to claim 11, wherein when the grasping portion is in the closed state, a gap having a predetermined distance is formed between a distal-end portion of the first jaw and a distal-end portion of the second jaw.

20. The medical system according to claim 11, wherein the first jaw includes a staple extraction portion wherein the second jaw includes a staple reception portion, wherein the second jaw is provided with a concave portion formed in at least part of a region in a direction from the staple reception portion to the rotation shaft, and wherein a distance between the first jaw to the concave portion is larger than a distance from the first jaw to other part of the second jaw.

\* \* \* \* \*